(12) United States Patent
Eisenkraetzer et al.

(10) Patent No.: US 11,866,686 B2
(45) Date of Patent: Jan. 9, 2024

(54) IDENTIFICATION OF CALIBRATION DEVIATIONS OF PH-MEASURING DEVICES

(71) Applicant: Hoffmann-La Roche, Inc., Little Falls, NJ (US)

(72) Inventors: Detlef Eisenkraetzer, Iffeldorf (DE); Christian Klinger, Penzberg (DE); Katrin Greppmair, Penzberg (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 17/575,008

(22) Filed: Jan. 13, 2022

(65) Prior Publication Data

US 2022/0325223 A1    Oct. 13, 2022

Related U.S. Application Data

(62) Division of application No. 15/765,222, filed as application No. PCT/EP2016/076173 on Oct. 28, 2016, now Pat. No. 11,371,006.

(30) Foreign Application Priority Data

Oct. 30, 2015 (EP) ..................... 15192389

(51) Int. Cl.
*G01N 27/416* (2006.01)
*C12M 1/34* (2006.01)
(Continued)

(52) U.S. Cl.
CPC ............ *C12M 41/26* (2013.01); *C12M 41/36* (2013.01); *G01D 18/008* (2013.01); *G01N 27/4165* (2013.01); *G05D 21/02* (2013.01)

(58) Field of Classification Search
CPC .... C12M 41/26; C12M 41/36; G01N 27/4165
See application file for complete search history.

(56) References Cited

U.S. PATENT DOCUMENTS 4,513,280 A   4/1985  Hannan et al.
5,578,194 A   11/1996 Young et al.
(Continued)

FOREIGN PATENT DOCUMENTS

CN   1557948 A   12/2004
CN   102191275 A   9/2011
(Continued)

OTHER PUBLICATIONS

H. Evans et al., Dealing with Disparity in On-line and Off-line pH measurements, Pharmanufacturing.com 1-4, 2006. (Year: 2006).*
(Continued)

*Primary Examiner* — Caitlyn Mingyun Sun
(74) *Attorney, Agent, or Firm* — Alston & Bird LLP

(57) ABSTRACT

The invention relates to a comparison unit (130) configured for determining if a first pH measuring device of a first tank (104; 106) is affected by a pH-measuring problem, the comparison unit being configured for:

receiving a first CO2 concentration and a first pH value, the first CO2 concentration being a CO2 concentration of a first gas volume above a medium in a first tank, the first CO2 concentration and the first pH value being measured at a first time when the medium in the first tank is in pH-CO2 equilibrium state with the first gas volume and before said equilibrium state is modified by the metabolism of a cell culture in the first tank, the first pH value being a measured value provided by a first pH measuring device operatively coupled to the first tank (102);

receiving a second CO2 concentration and a second pH value, the second CO2 concentration being a CO2 concentration of a second gas volume above a medium in a second tank, the second CO2 concentration and the second pH value being measured at a second time when
(Continued)

the medium in the second tank is in pH-CO2 equilibrium state with the second gas volume and before said equilibrium state is modified by the metabolism of a cell culture, the second pH value being a measured value provided by a second pH measuring device;

comparing the first and second pH values and CO2 concentrations for determining if comparing (206), by the comparison unit, the first and second pH values and comparing the first and second CO2 concentrations for determining if the first pH measuring device is affected by the pH-measuring problem.

20 Claims, 7 Drawing Sheets

(51) Int. Cl.
G01D 18/00 (2006.01)
G05D 21/02 (2006.01)

(56) References Cited

U.S. PATENT DOCUMENTS

| | | |
|---|---|---|
| 5,658,451 A | 8/1997 | Leiner |
| 6,123,827 A | 9/2000 | Wong et al. |
| 2004/0010186 A1 | 1/2004 | Kimball et al. |
| 2006/0155511 A1 | 7/2006 | Steinmueller et al. |
| 2006/0216818 A1 | 9/2006 | Amano |
| 2010/0120139 A1 | 5/2010 | Busujima et al. |
| 2010/0184147 A1 | 7/2010 | Cheng et al. |
| 2013/0115588 A1 | 5/2013 | Davis et al. |
| 2014/0141469 A1 | 1/2014 | Henderson et al. |
| 2014/0330398 A1 | 11/2014 | Fan et al. |
| 2015/0111252 A1 | 4/2015 | Hirschel et al. |
| 2017/0307563 A1 | 10/2017 | Okamura |

FOREIGN PATENT DOCUMENTS

| | | |
|---|---|---|
| EP | 0147975 A2 | 7/1985 |
| EP | 2365060 A1 | 9/2011 |
| JP | S60-141286 A | 7/1985 |
| JP | H06 174677 A | 6/1994 |
| JP | 2009-075088 A | 4/2009 |
| JP | 2011-160802 A | 8/2011 |
| JP | 2012-531930 A | 12/2012 |
| JP | 2013-019804 A | 1/2013 |
| JP | 2014-527824 A | 10/2014 |
| WO | WO 2007/085880 A1 | 8/2007 |
| WO | WO 2013/041487 A1 | 3/2013 |

OTHER PUBLICATIONS

European Application No. 16788131.7, Communication Under Rule 71(3) EPC dated Aug. 26, 2021.
Japanese Patent Application No. 2018-517792, Decision of Rejection dated Sep. 22, 2021.
Japanese Patent Application No. 2018-517792, Notice of Reasons for Rejection dated Nov. 30, 2020.
Summary of Chinese Office Action for Chinese Application No. 201680058166.6 dated Dec. 10, 2021.
WIPO Application No. PCT/EP2016/076167, PCT International Search Report and Written Opinion dated Jan. 26, 2017.
Definition of "calibrate", (2020).
Evans, H. et al., "Dealing with Disparity in On-Line and Off-line pH Measurements Genentech found pH drift in its on-line measurements for a cell culture process, and continues to investigate its cause," Pharmanufacturing.com, (Jan. 1, 2006) [Retrieved from the Internet May 10, 2016 <URL:https://www.pharmamanufacturing.com/assets/Media/MediaManager/genentech_ph-disparity-poster.pdf>].
Goudar, C.T., et al., "Decreased pCO2 accumulation by eliminating bicarbonate addition to high cell-density cultures," Biotechnology and Bioengineering, 96:1107-1117, (2007).
Gramer, M.J., et al., "A semi-empirical mathematical model useful for describing the relationship between carbon dioxide, pH, lactate and base in a bicarbonate-buffered cell-culture process," Biotechnology and Applied Biochemistry, 47(4):197-204, (Mar. 15, 2007).
Gros, J.B., et al., "Estimation of O2 and CO2 Solubility in Microbial Culture Media," Biotechnology Progress, 15:923-927, (1999).
Kamen, A., et al., On-Line Monitoring or Respiration in Recombinant-Baculovirus Infected and Uninfected Insect Cell Bioreactor Cultures, 50, Biotechnology and Bioengineering, 1996, 36-48.
Sazonov, V.P. ET AT., "Introduction to the solubility data series," IUPAC-NIST Solubility Database, NIST Standard Reference Database 106, 2006 [Retrieved from the Internet Jun. 27, 2018 <URL:http://srdata.nist.gov/solubitility/intro.aspx>].
Australian Patent Application No. 2016345668 Examination Report No. 1 dated Mar. 16, 2021.
Australian Patent Application No. 2016345668 Notice of Acceptance for Patent Application dated Jun. 25, 2021.
Brazilian Patent Application No. 112018003852-0, Preliminary Search Report and Written Opinion dated Jan. 3, 2020.
Chinese Patent Application No. 201680058528.1 First Office Action dated Dec. 2, 2021.
European Patent Application No. 20176613.6 Communication under Rule 71(3) EPC dated Dec. 8, 2021.
European Patent Application No. 20176613.6, Extended European Search Report dated Jan. 28, 2021.
Japan Patent Application No. 2018-517832, Notice of Reasons for Rejection dated Aug. 17, 2020.
PCT International Preliminary Report on Patentability Chapter II for PCT/EP2016/076173 dated Nov. 9, 2017.
PCT International Search Report and Written Opinion for PCT/EP2016/076173 dated Feb. 20, 2017.
Singapore Patent Application No. 11201801533T, Written Opinion dated Jun. 25, 2019.
Singapore Patent Application No. 11201801533T, Written Opinion dated Dec. 27, 2019.
U.S. Appl. No. 15/765,222, filed Mar. 30, 2018, 2018-0216059, Pending.

* cited by examiner

IDENTIFICATION OF CALIBRATION DEVIATIONS OF PH-MEASURING DEVICES

CROSS-REFERENCE TO RELATED APPLICATIONS

This application is a divisional of U.S. application Ser. No. 15/765,222 (published as US20180216059A1), filed Mar. 30, 2018, which application is a U.S. National Stage entry of International Application No. PCT/EP2016/076173, filed Oct. 28, 2016, which application claims the benefit of European Patent Application No. 15192389.3, filed Oct. 30, 2015, each of which is herein incorporated by reference in its entirety for all purposes.

FIELD OF THE INVENTION

The present invention relates to the field of using and calibrating pH measuring devices, and more particular to the identification of calibration errors and/or pH offset effects resulting from a sampling process.

BACKGROUND AND RELATED ART

Using accurately calibrated pH measuring devices is useful or critical in a great many situations, including chemical or biological laboratory work, for operating bioreactors, for monitoring harvest reactors, etc.

Bioreactors are commonly used for carrying out chemical processes, in particular processes performed by living organisms, in a controlled manner, e.g. in order to obtain a chemical compound, e.g. a particular peptide, protein, or other kind of chemical substance. A common goal is to operate the bioreactor in a way that the microorganisms or cells are able to perform their desired function with limited production of impurities and/or in a time- and cost-efficient manner. The environmental conditions inside the bioreactor, such as temperature, nutrient concentrations, pH, and dissolved gases, among other parameters, are typically chosen such that the growth and productivity of the organisms is optimized.

In order to determine if the state of a bioreactor and/or the state of a cell culture in a bioreactor is at a desired state, e.g. a state corresponding to a state of a reference bioreactor at a given moment in time when performing a cell culture project, the pH value is repeatedly measured. In case the pH value is outside a desired pH-value range, various parameters of the bioreactors (such as feed rate, aeration rate, temperature, stirring rate or the like) may be adapted to change the state of the bioreactor in a way that the measured pH value in the medium lies within the desired pH value range.

Various control parameters of a bioreactor may be set in dependence on a currently measured pH value in the medium of a bioreactor. The correct setting of said parameters determines if a particular cell culture will be cultivated under very similar/approximately identical conditions as a reference culture in another bioreactor. Therefore, in order to synchronize the state of a bioreactor with the state of another (reference) bioreactor, it is of crucial importance that the pH measuring devices of the two compared bioreactors output the same pH value for media having the same pH value.

Many other use case scenarios exist where the determination of the correct pH value is of crucial importance. For example, at the end of a cell culture project, the cell culture and/or its products can be stored in a harvest tank before they are further processed to extract the desired cell culture products. The harvest tanks need to be closely monitored to prevent or at least immediately identify any infection or other modification of the conditions within the harvest tank that could result in a degradation of its contents. Therefore, the pH value in harvest tanks is repeatedly measured by taking samples and measuring the pH value of the samples.

Often, tank-external pH measuring devices are used for measuring the pH value of a sample of the medium contained in a tank, e.g. a bioreactor or harvest tank. However, the process of withdrawing medium samples bears the risk of an infection of the tank. Moreover, the pH value measured in a sample may deviate from the actual pH value of the medium within the tank due to so called "offset effects". Offset effects may be caused, for example, during the process of withdrawing the sample and transporting it to the pH measuring device as the temperature of the sample, the environmental pressure or environmental air composition may differ from the respective parameters within the tank. This may result in a measured pH value in the sample that differs—due to offset effects—significantly from the actual pH value of the medium in the tank. As a consequent, the pH value measured in the sample does not accurately reflect the current state in the tank.

Wrongly calibrated pH measuring devices are a further potential source of error: typically, pH measuring devices are calibrated with commercially available reference solutions having a defined pH value. This approach typically requires the withdrawal and re-introduction of the pH measuring device from the tank. After re-introduction of the pH measuring device, the tank and the pH measuring device contained therein need to be autoclaved. This process may have an effect on the already calibrated pH measuring device, resulting in a pH measuring device in the tank that might indicate a different pH value for the reference solution than it did before autoclavation. Even in case the pH measuring device was not affected by the autoclavation process, there is no guarantee that the pH measuring device was unaffected by the autoclavation. As a result, the measured pH values may be not be considered as trustworthy and a re-calibration of the tank-internal pH meter may be performed to calibrate the tank-internal pH meter by using a tank-external reference pH meter that measures the pH in a sample of the medium of the tank. However, due to offset effects during the sampling process, this will also not guarantee that the tank-internal pH meter is calibrated correctly.

Regularly taking samples for performing offline pH measurements is burdensome and increases the risk of infecting the bioreactor with undesired germs.

SUMMARY

It is an objective of the present invention to provide for an improved system and method for determining if a pH measuring device is affected by a pH-measuring problem and for re-calibrating a pH meter as specified in the independent claims. Embodiments of the invention are given in the dependent claims. Embodiments of the present invention can be freely combined with each other if they are not mutually exclusive. Embodiments of the invention may take advantage of the ease with which a CO2 concentration in the air volume in a tank can be measured for improving and facilitating the identification of pH measuring problems and calibration problems. According to one beneficial aspect, CO2 concentrations measured in two or more different tanks may be used for identifying pH-measuring deviations of the pH measuring devices which are operatively coupled to the different tanks.

In one aspect, the invention relates to a method for determining if a first pH measuring device operatively coupled to a first tank is affected by a pH-measuring problem. The pH measuring problem is that the first pH measuring device is calibrated differently than a second pH measuring device operatively coupled to a second tank. For example, this situation can be problematic if the second tank is a reference bioreactor and the first tank is another bioreactor whose state shall be compared and synchronized with the state of the reference bioreactor. The method comprises:

receiving by a comparison unit, a first $CO_2$ concentration and a first pH value, the first $CO_2$ concentration being a $CO_2$ concentration of a first gas volume above a medium (M1) in the first tank, the first $CO_2$ concentration and the first pH value being measured at a first time, the first time being a time when the medium in the first tank is in pH-$CO_2$ equilibrium state with the first gas volume at a predefined temperature and pressure, said equilibrium state being unaffected by the metabolism of any cell culture, the first pH value being a measured value provided by the first pH measuring device (108; 146);

receiving, by the comparison unit, a second $CO_2$ concentration and a second pH value, the second $CO_2$ concentration being a $CO_2$ concentration of a second gas volume above the same type of medium (M1) contained in the second tank, the second $CO_2$ concentration and the second pH value being measured at a second time, the second time being a time when the medium in the second tank is in pH-$CO_2$ equilibrium state with the second gas volume at the predefined temperature and pressure, said equilibrium state being unaffected by the metabolism of any cell culture, the second pH value being a measured value provided by the second pH measuring device;

comparing, by the comparison unit, the first and second pH values and comparing the first and second $CO_2$ concentrations for determining if the first pH measuring device is affected by the pH-measuring problem.

According to embodiments, the determination that the first pH measuring device has a pH measuring problem is made in case:

first and second $CO_2$ concentrations are identical and the first and second pH values differ from each other by more than a threshold value; or the first and second pH values are identical and the first and second $CO_2$ concentrations differ from each other by more than a further threshold value; or a first data value differs from a second data value by more than a further threshold, the first data value being derived from the first pH value and the first $CO_2$ concentration, the second data value being derived from the second pH value and the second $CO_2$ concentration.

The first tank can be, for example, a bioreactor or a harvest tank. The second tank can be, for example a bioreactor, in particular a reference bioreactor, or a harvest tank, in particular a reference harvest tank.

Embodiments of the invention may be advantageous as they allow to more accurately compare the pH values of the media in two or more tanks, e.g. a reference tank and one or more monitored or controlled tanks. The reference pH profile of the reference tank may be obtained several days, weeks or years prior to obtaining the measurement values in the tank(s) to be monitored. Alternatively, the first and second tanks may be operated in a basically concurrent manner. In a further beneficial aspect, offline measurements of the pH can be omitted, thereby avoiding a contamination of the tanks and avoiding an inaccurate comparison of pH values as sampling effects may create a significant variability of the measured pH value.

According to a further beneficial aspect, $CO_2$ concentrations measured in a particular tank may be used for computing an absolute, expected pH value and may allow identifying any deviations of the actually measured pH value from the expected pH value. Said deviation may be an indicator for a pH measuring problem, e.g. a calibration problem.

In a further aspect, the invention relates to a method for determining if a first pH measuring device operatively coupled to a first tank is affected by a pH-measuring problem. The problem is that the first pH measuring device is calibrated wrongly (and thus does not only produce a pH value that is wrong relative to a pH value provided by a reference pH measuring device, but that produces a pH value that is wrong in absolute terms). The method comprises:

receiving, by a comparison unit, a first $CO_2$ concentration and a first pH value, the first $CO_2$ concentration being a $CO_2$ concentration of a first gas volume above a medium (M1) in the first tank, the first $CO_2$ concentration and the first pH value being measured at a first time, the first time being a time when the medium in the first tank is in pH-$CO_2$ equilibrium state with the first gas volume at a predefined temperature and pressure, said equilibrium state being unaffected by the metabolism of any cell culture, the first pH value being a measured value provided by the first pH measuring device;

computing, by the comparison unit, a second pH value as a function of the first $CO_2$ concentration, the second pH value being the pH value predicted for said type of medium (M1) when said medium is in pH-$CO_2$ equilibrium state with a second gas volume above said medium (M1) at the predefined temperature and pressure, the second gas volume in said equilibrium having a second $CO_2$ concentration that is identical to the first $CO_2$ concentration, said equilibrium state being unaffected by the metabolism of any cell culture;

comparing, by the comparison unit, the first and second pH values for determining if the first pH measuring device is affected by the pH-measuring problem.

This may be advantageous as this method allows to determine, provided some properties of the medium are known, the correct, absolute pH value of the medium using the $CO_2$ concentration in the air volume of the tank that may be measured in the offgas as input. By comparing the computed, accurate pH value derived from the $CO_2$ concentration with the actually measured pH value, it is possible to detect calibration errors.

According to embodiments, the comparison unit outputs a warning signal that in case it was determined that the first pH measuring device is affected by the pH measuring problem. This may allow an operator to take appropriate action, e.g. re-calibrate the pH measuring device, replace the pH measuring device, etc.

Computing an Expected pH Value Using the Offgas $CO_2$ Concentration

According to some examples related to the use of "minimalistic" media, e.g. salt solutions being basically free of substances acting as a buffer, the calculation of a pH value based on carbon dioxide in the gas phase in carbonate buffered systems can be performed as follows:

The concentration of carbon dioxide that is dissolved in a liquid is proportional to carbon dioxide partial pressure (pCO2) in the gas phase and can be calculated using respective proportional factors. Proportional factors depend on the liquid and temperature as well as pressure.

For example, the solubility coefficient for CO2 in various liquids is known and can be derived from literature or can be determined experimentally. The solubility coefficient in blood at 37 degC. is about 0.0304 mmol×L−1×mmHg−1 [Löffler, G., Petrides, P. E., Physiologische Chemie, Springer-Verlag, volume 4, 1990, p. 24]. According to Sazonov and Shaw, the Bunsen coefficient is defined as the volume of saturating gas reduced 273.15 and 1 bar, which is absorbed by unit volume of pure solvent at the temperature of measurement and partial pressure of 1 bar. Dimension is therefore volume/volume or dimensionless. This coefficient is based on Henry's Law, claiming that in equilibrium the partial pressure of a gas is directly proportional to the concentration of this gas that is solved in a correlated solution. Solubility coefficients depend on the respective solution [Gros, J. B., Dussap, C. G., Catté, M., Estimation of O2 and CO2 solubility in microbial culture media. Biotechnology Progress 1999, 15, 923-927].

If the solubility coefficient of a medium is known, concentration of dissolved carbon dioxide can be calculated by carbon dioxide concentrations in the gas phase. Concentrations in the gas phase, e.g. in bioreactors, can be directly measured using an off gas analyzer.

Carbon Dioxide and Carbonic Acid-Base Equilibria $$CO_{2(g)} \rightarrow CO_{2(aq)} \qquad \text{Equation 1}$$

Dissolved $CO_{2(aq)}$ is hydrated in water ($H_2O$) to carbonic acid ($H_2CO_3$).

$$CO_{2(aq)} + H_2O \leftrightharpoons H_2CO_3 \qquad \text{Equation 2}$$

In aqueous solutions at neutral pH and 37 degC hydrated species carbonic acid is almost nonexistent; both species therefore can be combined to H2CO3*(CO2(aq)+H2CO3=H2CO3). At typical fermentation pH around 7.00, $H_2CO_3^*$ dissociates to bicarbonate (HCO3−) and a proton (H+). Carbonate (CO32−), the deprotonated species is almost nonexistent at neutral pH values.

Aqueous $CO_2$ (aq) can dissolve limestone $$CaCO_3 + CO_2(aq) + H_2O \leftrightharpoons Ca^{2+}(aq) + 2HCO_3^-(aq)$$

and can react with the water to form carbonic acid $$CO_2(aq) + H_2O \leftrightharpoons H_2CO_3(aq)$$

Only a small fraction exists as the acid, so the dissociation constant K is $$K = \frac{[H_2CO_3(aq)]}{[CO_2(aq)]}.$$

Carbon Dioxide and Carbonic Acid-Base Equilibria

Dissolved CO2 in the form of H2CO3 may loose up to two protons through the acid equilibria $$H_2CO^*_3 \leftrightharpoons HCO_3^- + H^+ \quad K_{S1}=10^{-6.35} \qquad \text{Equation 3}$$

$$HCO_3^- \leftrightharpoons CO_3^{2-} + H^+ \quad K_{S2}=10^{-10.33} \qquad \text{Equation 4}$$

Dissociation constants $K_{S1}$ and $K_{S2}$, are given here for standard conditions (298, 15 K, ion strength $I_c$=0 M) [Goudar, C. T. C., Matanguihan, R., Long, E., Cruz, C., et al., Decreased pCO2 accumulation by eliminating bicarbonate addition to high cell-density cultures. *Biotechnology and Bioengineering* 2007, 96, 1107-1117].

For cell culture conditions temperatures of 37 degC as well as ion strengths of 0.1 M can be used. This will change the respective dissociation constants to $10^{-6.07}$ and $10^{-10.04}$, respectively.

Ratio of all species carbon dioxide ($H_2CO_3^*$), bicarbonate $HCO_3^-$ and carbonate $CO_3^{2-}$ can be calculated using the Henderson-Hasselbalch-Equation.

Equilibrium equations:

$$K_{S1} = \frac{[H^+][HCO_3^-]}{[H_2CO_3]} \qquad \text{Equation 5}$$

$$K_{S2} = \frac{[H^+][CO_3^{2-}]}{[H_2CO_3^-]} \qquad \text{Equation 6}$$

Acid equilibrium equations can be solved to give the fraction ∝ of respective carbonates as a function of proton concentration, hence pH:

$$\propto_{H_2CO_3} = \frac{[H^+]^2}{[H^+]^2 + [H^+]*K_{S1} + K_{S1}K_{S2}} \qquad \text{Equation 7}$$

$$\propto_{HCO_3^-} = \frac{[H^+]*K_{S1}}{[H^+]^2 + [H^+]*K_{S1} + K_{S1}K_{S2}} \qquad \text{Equation 8}$$

$$\propto_{HCO_3^-} = \frac{K_{S1}K_{S2}}{[H^+]^2 + [H^+]*K_{S1} + K_{S1}K_{S2}} \qquad \text{Equation 9}$$

Relative H2CO3 concentration is in effect CO2 (aq) in equilibrium with water.

Computing the pH

In the following, an exemplary computation of an expected pH based on carbon dioxide concentration in water at 37 degrees Celsius will be described:

If carbon dioxide concentration in gas phase is known, dissolved carbon dioxide concentration can be calculated by the use of the Bunsen coefficient, valid at atmospheric pressure at 37 degC [Löffler, G., Petrides, P. E., Physiologische Chemie, Springer-Verlag, volume 4, 1990, p. 24].

$CO_{2aq}$=0.0304 [mmol/L*mmHg]*pressure*carbon dioxide concentration gaseousphase/100.

The pressure in this case is atmospheric pressure of 750.06 mmHg.

There may be 10% carbon dioxide in the gas phase of a tank. The carbon dioxide is given in [%]. The partial pressure of $CO_2$ in mmol/L ($CO_{2áq}$ [mmol/L]) is in this case computed according to 750.06 mmHg*10%/100=75,006 mmHg. We have then mmol/L $CO_{2áq}$.

Then, the proton concentration of the first equation H2CO3→H++HCO3− is computed via equation 5 and equation 6:

$H^+$ concentration equation 5=1,01468E−06 mmol/L.
$H^+$ concentration equation 6=1,06941E−10 mmol/L.
The overall $H^+$ concentration therefore is 1,01468E−06 mmol/L+1,06941E-10 mmol/L=1,01479E−06 mmol/L.

The contribution of equation 5 to the overall H⁺ concentration is larger than that of equation 6.

pH is then computed according to pH=−log(1,01479E−06)=5,99.

The $CO_2$ concentration in the gas phase can be computed based on bicarbonate concentration and pH according to:

$$CO_2[\%] = \frac{\left\{\left(\frac{[10^{-pH}]^2}{[10^{-pH}]^2 + [10^{-pH}]*K_{S1} + K_{S1}K_{S2}}\right)*C\right\}}{750.06 \text{ mmHg}} * 100$$

With b being the Bunsen coefficient of 0.0304 mmol/L*mmHg at normal atmospheric pressure of 750.06 mmHg, pH being the pH value of solution, and C being the concentration of bicarbonate in [mmol/L].

First, the amount of $CO_2$ dissolved in water (aq) under normal atmosphere of pressure is computed using Henry's Law $$[CO2(aq)]=K_{CO2}*H, \quad \text{Equation 10}$$

wherein $K_{CO2}$ is the $CO_2$ concentration measured in the gas phase/offgas and H is the Henry solubility.

After having determined [CO2(aq)] (equation 10) and $K_{s1}$ (equation 5), the formula $$K_{S1} = \frac{[H^+]^2}{[CO2(aq)]} \quad \text{Equation 11}$$

Can be resolved for computing the pH as $$pH = \log_{10}([H^+]) = \log_{10}(\sqrt{K_{S1}[CO2(aq)]}).$$

Computing the Expected pH Value Using a Medium Specific Relation

According to embodiments, the comparison unit, for computing of the second pH value, reads a medium-specific relation from a data storage medium. The medium-specific relation is specific for the medium M1 of the first tank and indicates a relation between the pH value of the medium M1 and a respective fraction of $CO_2$ gas in a gas volume when said medium is in pH-CO2 equilibrium state with said gas volume and lacks a cell culture. The comparison unit inputs the first $CO_2$ concentration into the medium specific relation for calculating an absolute pH value expected for the medium in pH-CO2 equilibrium at the predefined temperature and pressure and under the absence of a cell culture. The absolute pH value is used as the computed second pH value.

This may be advantageous as a medium specific relation that correlates the pH value in the medium with a $CO_2$ concentration in the offgas in CO2-pH equilibrium state can be obtained empirically for any kind of medium, including media comprising a plurality of substances which have an impact on the pH-CO2 equilibrium.

According to embodiments, the medium-specific relation is an equation $PPH_{M1}(CO2)=REL\text{-}M1\ (CO2)$ obtained by mathematically fitting multiple empirically determined pairs of a pH-value of the medium (M1) and a respectively measured fraction of $CO_2$ gas in a gas volume. $PPH_{M1}$ (CO2) is the predicted pH value in a medium (M1) when said medium lacks a cell culture and is at pH-CO2 equilibrium with a gas volume above said medium, said gas volume comprising the $CO_2$ concentration used as input parameter.

The $CO_2$ is an input parameter value and represents the $CO_2$ concentration in a gas volume above the medium (M1) in pH-CO2 equilibrium state under the absence of the cell culture. REL-M1 is a set of one or more parameters (a1, a2, b1, b2, b3) connected by operators. The parameters have been obtained empirically by a method comprising:

adjusting samples of the medium (M1) lacking the cell culture to multiple different pH values, thereby letting the samples reach pH-CO2 equilibrium with the gas volume above the medium in the respective sample, determining the fraction of $CO_2$ gas in a in respective gas volume being in ph-CO2 equilibrium with the medium in the samples, plotting the determined $CO_2$ gas fractions against the respective equilibrium pH values of the samples, fitting a curve in the plotted values and deriving the parameters (a1, a2 or b1, b2, b3) of the medium-specific relation from the fitted curve.

For example, the medium specific relation can be determined in a special container or bioreactor that comprises a $CO_2$ offgas sensor and an online pH measuring device. The conditions used for determining the medium specific relation, e.g. temperature and pressure, are preferentially the same or very similar to the temperature and pressure prevailing when measuring the first pH value.

According to embodiments, the medium M1 in the tank whose pH value is measured is a medium of defined composition that is known to have the same composition like the medium used for empirically generating the medium-specific relation. For example, the medium in the tank and the medium used for generating the medium specific relation may be prepared by the operator of the tank or may be retrieved from a provider who discloses all components of the medium and the respective concentrations. Thus, the expressions "same type of medium" or the "same medium" as used herein both refer to media having the same composition at least in respect to all components having an impact on the pH-CO2 equilibrium.

For example, the medium may be a bicarbonate buffer that is free of any other substances (except the bicarbonate) which have an impact on the pH-CO2 equilibrium. Some providers of commercially available media do not disclose the complete list of ingredients. By preparing the buffer having a defined, limited set of components, the operator of a tank may ensure that the medium in the tank has exactly the same composition like the medium used for generating the medium specific relation. This may prevent an erroneous detection of a pH measuring problem or could the missing of a real pH measuring problem.

According to embodiments, the determination that the first pH measuring device has a pH measuring problem is made in case the first and second pH values differ from each other by more than a threshold value. Likewise, the determination that the first pH measuring device has a pH measuring problem is made in case a first data value differs from a second data value by more than a further threshold, the first data value being derived from the first pH value, the second data value being derived from the second pH value. For example, the threshold may be set by an operator of the tank to which the first pH measuring device is coupled and may depend on the accuracy requirements of the operator or the project for which the tank and the medium is used.

According to embodiments, the first tank is a bioreactor or a harvest tank or a calibration box.

According to a further beneficial aspect, CO2 concentrations measured in a particular tank may be used for calibrating or re-calibrating an erroneously calibrated pH measuring device.

In a further aspect, the invention relates to a method for calibrating or re-calibrating a first pH measuring device. The method comprises comparing pH values and CO2 concentrations measured in the first and in the second tank as described above for embodiments of the invention for determining that the first pH measuring device is affected by a pH-measuring problem; and calibrating the first pH measuring device such that it outputs the same pH value like the second pH measuring device in case the first and second CO2 concentrations are identical. Alternatively, the method comprises computing an expected second pH value from a first CO2 concentration measured in the offgas of a first tank as described above for embodiments of the invention for determining that the first pH measuring device in the first tank is affected by a pH-measuring problem; and calibrating the first pH measuring device such that it outputs the same pH value like the pH value computed as a function of the first CO2 concentration.

According to a further beneficial aspect, CO2 concentrations measured in a particular tank may be used for calibrating or re-calibrating an erroneously calibrated pH measuring device without removing and re-inserting the pH measuring device from and to the tank.

In a further aspect, the invention relates to a method of operating a tank comprising a first pH measuring device. The first pH measuring device is an online measuring device, the method comprising:
- growing a cell culture in the tank, the tank comprising a growth medium, thereby repeatedly measuring the pH in the growth medium by the first pH measuring device;
- replacing the growth medium and the cell culture contained therein in the tank with a medium (M1) for which a relation between pH and CO2 in equilibrium is known; for example, said medium M1 may be a medium whose corresponding medium-specific relation is stored in a data storage medium accessible to a comparison unit that performs the determination if a pH measuring problem exists, or the medium M1 may be a solely bicarbonate-buffered medium allowing the computation of the absolute pH value from the CO2 offgas concentration at pH-CO2 equilibrium;
- after having replaced the growth medium, computing an expected second pH value from the measured CO2 off gas concentration as described above for embodiments of the invention for determining that the first pH measuring device is affected by a pH-measuring problem;
- if a pH measuring problem was detected, calibrating the first pH measuring device such that it outputs the same pH value like the pH value computed as a function of the first CO2 concentration for the medium (M1);
- after having calibrated the first pH measuring device, replacing the medium in the tank with the growth medium.

Said features may be advantageous as it is not necessary any more to withdraw the pH measuring device from the tank, execute some calibration tests, optionally recalibrate it, autoclave the pH meter and reintroduce the autoclaved pH meter into the tank. Rather, the pH measuring device, which may be an online pH measuring device located within the tank, can be checked and re-calibrated in the tank. This may reduce the contamination risk and save time.

According to a further beneficial aspect, CO2 concentrations measured in a particular tank may be used for identifying pH offset effects caused by taking a sample of the medium in the tank.

In a further aspect, the invention relates to a method of determining pH offset effects caused by taking a medium sample from a first tank. The method comprising providing a tank-external, offline pH measuring device (160) and providing the first tank. The first tank comprises a first pH measuring device. The first pH measuring device is an online pH measuring device located within the first tank and is at least partially surrounded by the medium (M1) in the first tank. The method further comprises:
- calibrating the first (tank-internal) pH measuring device by computing a predicted, absolute pH value from a measured CO2 offgas concentration of the first tank for determining if the first (tank-internal) pH measuring device is affected by a pH-measuring problem; and calibrating (if a pH measuring problem was detected) the first (tank-internal) pH measuring device such that it outputs the same pH value like the pH value computed as a function of the first CO2 concentration;
- transferring the tank-external, offline pH measuring device into a calibration box comprising the same type of medium (M1) as the first tank; and calibrating (if a pH measuring problem was detected) the tank-external, offline pH measuring device by computing a predicted, absolute pH value from a measured CO2 offgas concentration of the calibration box for determining if the tank-external, offline pH measuring device is affected by a pH-measuring problem; and calibrating (if a pH measuring problem was detected) the tank-external, offline pH measuring device such that it outputs the same pH value like the pH value computed as a function of the CO2 concentration measured in the off gas of the calibration box; thus, the calibration box is used as the tank comprising the pH measuring device to be calibrated and is used as a container whose CO2 offgas sensor is used for measuring the CO2 concentration used as input for computing the second pH value to be used for calibrating the tank-external, offline pH measuring device.

After having calibrated the first pH measuring device and the tank-external pH measuring device, the method comprises:
- measuring, by the first pH measuring device, a first current pH value of the medium in the first tank, the first current pH value being an online-measurement value;
- taking a sample of the medium of the first tank and filling the sample into a portable container (162);
- positioning the tank-external pH measuring device such that it is at least partially surrounded with the medium in the sample container;
- measuring, by the tank-external pH measuring device, a second current pH value of the medium in the sample container, the second current pH value being an offline-measurement value;
- in case the first and the second current pH values differ by more than a threshold, determining that the sampling process caused an pH offset effect.

According to embodiments, the method further comprises:
- receiving a third CO2 concentration and a third pH value, the third CO2 concentration being a CO2 concentration of a third gas volume above the medium in the first tank, the third CO2 concentration and the third pH value being measured at a third time, the third time being a time when the medium in the first tank is in pH-CO2 equilibrium state at a predefined temperature and pressure with the third gas volume and after said equilibrium state is modified by the metabolism of the cell culture in the first tank, the third pH value being a measured value provided by the first pH measuring device;

receiving a fourth CO2 concentration and a fourth pH value, the fourth CO2 concentration being a CO2 concentration of a fourth gas volume above the medium in the second tank, the fourth CO2 concentration and the fourth pH value being measured at a fourth time, the fourth time being a time when the medium in the second tank is in pH-CO2 equilibrium state at the predefined temperature and pressure with the second gas volume and after said equilibrium state is modified by the metabolism of the cell culture in the second tank, the fourth pH value being a measured value provided by the second pH measuring device, the lapsed time between the third time and the inoculation of the first tank being identical to the lapsed time between the fourth time and the inoculation of the second tank;

receiving a measured first oxygen uptake rate of the cell culture in the first tank at the third time;

receiving a measured second oxygen uptake rate of the cell culture in the second tank at the fourth time;

in case the first and second oxygen uptake rates are identical, comparing the third and fourth pH values and CO2 concentrations for determining if the first and second pH measuring devices are calibrated differently.

For example, said steps may be performed by a comparison unit, e.g. a piece of program logic that monitors and/or controls the pH measurements and calibration states of one or more pH measuring devices. In addition, the comparison unit or a control unit coupled to the comparison unit may monitor and/or control the state of one or more tanks.

Accurately measuring and minimizing offset effects of a sampling process may be highly advantageous as the pH value measured in a sample may often be used as an important control parameter of bioreactors. The pH value measured in a sample of the medium of a bioreactor may often be the basis for taking corrective actions, e.g. for adding a basic substance, increasing or decreasing the temperature or feed rate may be performed. By calibrating the tank-internal pH measuring device as well as the tank-external pH measuring device based on a measured CO2 concentration, both pH measuring devices can be calibrated with respect to a highly accurate, absolute pH value that can be derived exactly from the CO2 concentration. Thus, calibration differences can be minimized. As a consequence, when operating the tank and regularly taking media samples, any difference in the pH value of the tank-internal pH measuring device and the tank-external pH measuring device can clearly be ascribed to sampling effects, not to calibration differences. Thus, the effect of the sampling process can be determined more accurately and can be filtered out (e.g. by computationally adding or subtracting the pH difference caused by the sampling process) from the pH value measured by the tank-external pH measuring device.

According to embodiments, the first pH measuring device is at least partially surrounded by the medium within the first tank. The first tank lacks means for manually or automatically taking a sample of the medium in the second tank. Alternatively, the first tank comprises means for manually or automatically taking a sample of the medium in the first tank, but all openings of the sampling means are kept close during a time interval after filling the medium in the first tank and before adding a cell culture to the medium in the first tank. This may reduce the risk of contaminating the tank with microbes.

According to embodiments, the second pH measuring device is at least partially surrounded by the medium within the second tank. The second tank lacks means for manually or automatically taking a sample of the medium in the second tank.

Alternatively, the second tank comprises means for manually or automatically taking a sample of the medium in the second tank, but all openings of the sampling means are kept close during a time interval after filling the medium in the second tank and before adding a cell culture to the medium in the second tank.

According to embodiments, the method for determining pH measuring problems described herein for embodiments of the invention used for determining if the second pH measuring device is calibrated differently than the first pH measuring device, the determination if the first and second pH measuring device are calibrated differently being performed while the second pH measuring device is at least partially surrounded with the medium in the second tank and without taking a sample of the medium of the second tank for performing said determination.

According to embodiments, comparing the pH values measured by two or more different pH measuring devices, the determination if the first pH measuring device is affected by a pH measuring problem is performed by using the first and second CO2 concentrations and the first and second pH values as the only data input for said determination.

According to embodiments, comparing the pH value measured by a particular pH measuring device with an expected pH value computed from the measured CO2 concentration, the determination if the first pH measuring device is affected by a pH measuring problem is performed by using the measured pH value and the measured CO2 concentration of the tank comprising said pH measuring device as the only data input for said determination.

Said features may be advantageous as no offline-measurements may be required any more for determining pH measuring problems.

According to embodiments, the measuring of the first pH value is performed as an online-measurement and the first pH measuring device is at least partially surrounded with the medium in the first tank. In this case, the first pH measuring device being operatively coupled to the first tank is a tank-internal pH measuring device of the first tank.

In addition, or alternatively, the measuring of the second pH value is performed as an online measurement and the second pH measuring device is at least partially surrounded by the medium in the second tank. In this case, the second pH measuring device being operatively coupled to the second tank is a tank-internal pH measuring device of the second tank.

According to embodiments, the measuring of the first CO2 concentration is performed as an online-measurement by a first CO2 sensor in the off gas of the first tank for providing the first CO2 concentration.

According to embodiments, the measuring of the second CO2 concentration is performed as an online-measurement by a second CO2 sensor in the off gas of the second tank for providing the second CO2 concentration.

According to embodiments, the comparison unit performs, in case of determining that the first pH measuring device is affected by a pH measuring problem, one or more of the following steps: outputting a warning message; automatically performing or triggering the performing of a recalibration of the first pH measuring device; or automatically performing or triggering the performing of a replacement of the first pH measuring device by a new first pH measuring device.

According to embodiments, the first tank differs from the second tank in respect to one or more of the following features:
  a) the gas volume in the tank,
  b) the medium volume in the tank,
  c) the Reynolds number of the tank,
  d) the Newton number of the tank,
  e) the dimensions of the tank,
  f) geometrical features of the tank and/or tank baffles,
  g) the stirrer configuration,
  h) the stirring rate,
  i) the volumetric mass transfer coefficient for oxygen (kLa) of the tank,
  j) total gas influx rate and/or O2 influx rate and/or N2 influx rate and/or CO2 influx rate,
  k) power input,
  l) pressure in the tank,
  m) gas bubble hold time in the medium,
  n) gas bubble size and distribution in the medium,
  o) surface speed,
  p) a parameter calculated as a derivative from one or more of the parameters a)-o);
  q) the geographic location of the two tanks.

In a further aspect, the invention relates to a comparison unit configured for:
  receiving, a first CO2 concentration and a first pH value, the first CO2 concentration being a CO2 concentration of a first gas volume above a medium (M1) in a first tank, the first CO2 concentration and the first pH value being measured at a first time, the first time being a time when the medium in the first tank is in pH-CO2 equilibrium state with the first gas volume at a predefined temperature and pressure, said equilibrium state being unaffected by the metabolism of any cell culture, the first pH value being a measured value provided by the first pH measuring device;
  receiving a second CO2 concentration and a second pH value, the second CO2 concentration being a CO2 concentration of a second gas volume above the same type of medium (M1) contained in the second tank, the second CO2 concentration and the second pH value being measured at a second time, the second time being a time when the medium in the second tank is in pH-CO2 equilibrium state with the second gas volume at the predefined temperature and pressure, said equilibrium state being unaffected by the metabolism of any cell culture, the second pH value being a measured value provided by the second pH measuring device;
  comparing the first and second pH values and comparing the first and second CO2 concentrations for determining if the first pH measuring device is affected by the pH-measuring problem.

In a further aspect, the invention relates to a comparison unit configured for:
  receiving a first CO2 concentration and a first pH value, the first CO2 concentration being a CO2 concentration of a first gas volume above a medium (M1) in a first tank, the first CO2 concentration and the first pH value being measured at a first time, the first time being a time when the medium in the first tank is in pH-CO2 equilibrium state with the first gas volume at a predefined temperature and pressure, said equilibrium state being unaffected by the metabolism of any cell culture, the first pH value being a measured value provided by the first pH measuring device;
  computing a second pH value as a function of the first CO2 concentration, the second pH value being the pH value predicted for said type of medium (M1) when said medium is in pH-CO2 equilibrium state with a second gas volume above said medium (M1) at the predefined temperature and pressure, the second gas volume in said equilibrium having a second CO2 concentration that is identical to the first CO2 concentration, said equilibrium state being unaffected by the metabolism of any cell culture;
  comparing the first and second pH values for determining if the first pH measuring device is affected by the pH-measuring problem.

In a further aspect, the invention relates to a system configured for monitoring and/or controlling a state of a first tank. The system comprises:
  the comparison unit according to embodiments of the invention;
  a control unit operatively coupled to the comparison unit; and
  the first tank and the first pH measuring device;
  the control unit being configured to monitor and/or control a state of a cell culture in the first tank, thereby using pH values repeatedly measured by the first pH measuring device as input.

According to embodiments, the system is configured for using pH values of the first and second pH measuring device and the first and second CO2 concentrations as an input parameter for monitoring and/or minimizing deviations of a state of the first tank from the state of the second tank by analyzing at least said input parameters.

In the following, embodiments and examples will be described by making reference to bioreactors. However, bioreactors are only one type of tank where embodiments of the invention may be applied. Other examples are harvest tanks and calibration boxes.

In one aspect, the invention relates to a method comprising:
  receiving, by a comparison unit, a first CO2 concentration and a first pH value. The first CO2 concentration is a CO2 concentration of a first gas volume above a medium in the first bioreactor. The first CO2 concentration and the first pH value are measured at a first time. The first time is a time when the medium in the first bioreactor is in pH-CO2 equilibrium state at a predefined temperature and pressure with the first gas volume and before said equilibrium state is modified by the metabolism of a cell culture in the first bioreactor. The first pH value is a measured value provided by a first pH measuring device operatively coupled to a first bioreactor;
  receiving, by the comparison unit, a second CO2 concentration and a second pH value. The second CO2 concentration is a CO2 concentration of a second gas volume above a medium in the second bioreactor. The second CO2 concentration and the second pH value are measured at a second time. The second time is a time when the medium in the second bioreactor is in pH-CO2 equilibrium state at the predefined temperature and pressure with the second gas volume and before said equilibrium state is modified by the metabolism of a cell culture in the second bioreactor. The second pH value is a measured value provided by a second pH measuring device operatively coupled to a second bioreactor. The medium in the first bioreactor is the same as the medium in the second bioreactor;

comparing, by the comparison unit, the first and second pH values and the second $CO_2$ concentrations for determining if the first and second pH measuring devices are calibrated differently or for determining if the first and second pH measuring devices output different pH values due to offset effects of a sampling process performed for measuring the first or second pH value in a sample of the medium of a respective one of the first and second bioreactors.

For example, the second bioreactor may be used as a reference bioreactor and the first bioreactor may be used as another bioreactor in which a cell culture project shall be run basically in the same way as a reference cell culture having been cultivated previously in the reference bioreactor. It may also be the case that the first and second bioreactors shall be run synchronously, whereby the respective pH values are repeatedly measured in order to compare the state of the bioreactors. The parameter comparison may be performed, for example, in order to automatically, semi-automatically or manually initiate appropriate actions in order to prevent a state deviation of said two bioreactors.

It has been observed that calibration errors of the first or second pH measuring devices are common error sources resulting in a failure to accurately compare the states of the two bioreactors and/or to accurately reproduce a state profile derived from the second bioreactor in the first bioreactor. Calibration errors are common error sources both for offline and online pH measurement approaches.

Further, it has been observed that in case offline pH measurements are performed in the first and/or second bioreactor, the obtained offline pH value may not accurately reflect the current pH value of the medium in the bioreactor. For example, a medium sample may be regularly drawn from a bioreactor in order to regularly perform an offline pH measurement in said samples. The sampling process before the pH value can be measured in the medium sample takes time. In the meantime, the pH value in the bioreactor from which the sample was drawn may have significantly changed. Further, it may happen that the temperature in the sample drops during the sampling process, or the pH value in the sample shifts due to a change in the $CO_2$ concentration in the gas volume above the medium of the sample compared to the gas volume above the medium in the bioreactor. All said factors may influence the pH value in the medium sample and lead to a so called "offset effect".

An "offset effect" as used herein is a pH value offset by which a pH value measured in a medium sample of a bioreactor at a particular time differs from a pH value that would be measured at said particular time directly in the medium of the bioreactor. Thus, calibration errors of the first or second pH measuring device and/or offset effects (in case the first and/or second pH measuring device is an offline measuring device) may result in a failure to accurately compare and/or synchronize the state of two bioreactors based on pH measurement values.

Embodiments of the invention take advantage of the fact that in case two identical solutions/media are in pH-$CO_2$ equilibrium state at a given temperature and pressure and a given pH value, the volume above said media have the same $CO_2$ concentration. Likewise, given a particular $CO_2$ concentration in the volumes above said two media in equilibrium state, the pH values of said two media are identical as a consequence of the two media being in pH-$CO_2$ equilibrium. As the two media are free of any cells whose metabolism could shift the pH-$CO_2$ equilibrium state, any deviation of the first and second pH value given identical measured $CO_2$ concentrations is used as an indication that the two pH measuring devices are calibrated differently and/or that the difference is caused by an offset effect of an offline pH measurement.

For example, the "predefined" or "given" temperature of the second bioreactor can be any temperature and pressure that is suitable for initiating and/or operating the second bioreactor. For example, the second temperature could be 20° C. and the second pressure could be normal atmospheric pressure. The second temperature and pressure may be measured and the temperature and pressure of the first bioreactor (referred herein as "first temperature" and "first pressure" can be controlled and adapted such that the first and second temperatures are identical or approximately identical and the first and second pressures are identical or approximately identical.

Embodiments of the invention may be advantageous for multiple reasons:

The comparison of the $CO_2$ concentrations and the pH values at a time before the pH value of the medium is affected by any metabolic activities of the cell culture allows to check if the first pH measuring device is calibrated differently than the second pH measuring device and allows determining, in case one or both of said pH measuring devices are offline-devices, if one or both of the measured pH values may be flawed by an offset effect.

An early detection of calibration differences and/or offset effects may allow recalibrating, repairing or exchanging the pH measuring device before the medium is inoculated with the cell culture. The recalibrating may include the option to calibrate the first pH measuring device such that it compensates for any offset effect. Thus, growing a cell culture in a bioreactor whose pH measuring device is calibrated differently than a pH measuring device of a reference bioreactor (or whose measured pH values are flawed by an offset effect) can be avoided and/or corrected from the beginning, thereby saving time and money that would be lost in case a calibration error of a pH measuring device results in a failure to reproduce the environmental conditions of the reference ("second") bioreactor in the other ("first") bioreactor.

In a further beneficial aspect, embodiments of the invention allow comparing pH values of different bioreactors even in case the two compared bioreactors and respective pH measuring devices are located far apart from each other, e.g. are located in different buildings or different cities or even different countries. Instead of relying on standardized, commercially available calibration solutions having a defined pH value, the $CO_2$ value (which can easily and highly accurately be determined) is used as basis for comparing the measured pH values and for identifying calibration differences and/or offset effects in a pH measurement. The measured first $CO_2$ concentration and the first measured pH value can be communicated to the comparison unit easily, e.g. via an internet connection. It is not necessary that the first and second pH measuring devices are calibrated and compared at the same time. It is not even necessary that the absolute pH value is correctly determined, Given a first pH value and a first $CO_2$ value measured by a first pH measuring device in a first bioreactor at pH-$CO_2$ equilibrium state as described above, it is possible to determine, by measuring a second pH value and second $CO_2$ value by a second pH measuring device in a second bioreactor at pH-$CO_2$ equilibrium state as described above, if the first and second pH measuring devices are calibrated identically, even in case the second pH value and second CO2 value were determined weeks or years before the first pH value and second CO2 values were observed.

In a further aspect, in case the first bioreactor shall be operated basically with the same environmental parameters like the second bioreactor, determining the absence of calibration differences of the second and first pH measuring devices and determining the absence of offset effects in the pH measurements may be much more important than a correct measurement of an absolute pH value. So even in case the second bioreactor (whose operational parameters may provide a kind of "reference profile" for operating the first bioreactor) was operated with a wrongly calibrated pH measuring device and/or the second pH value is influenced by an offset effect while the first pH measuring device (of the first bioreactor that shall be operated as specified in the "reference profile") is calibrated correctly/has no offset effect, embodiments of the invention allow to identify a calibration difference and/or the existence of an offset effect when measuring the second pH measuring device. The identification of the calibration difference and/or offset effect when measuring the second or first pH value allows an operator or an automated control system to take appropriate actions to prevent growing of the cell culture in the first bioreactor under different environmental parameters (in particular, under different pH values of the medium) than the cells of the second/reference bioreactor.

Thus, embodiments of the invention may enable accurate monitoring and/or controlling of the state of a bioreactor by identifying pH measuring device calibration differences and/or offset effects already at the initialization phase of a bioreactor.

According to other embodiments, the first bioreactor comprises means for manually or automatically taking a sample of the medium in the first bioreactor. During a time interval after filling the medium in the first bioreactor and before adding the cell culture to the medium in the first bioreactor, the method comprises keeping all openings of the sampling means closed.

This may be beneficial as a contamination of the medium of the first bioreactor is avoided. Opening of the sampling means for determining the pH value in a reference solution of known pH value is not necessary any more: calibration differences are identified via the CO2 values and the pH values are measured, according to embodiments of the invention, by the pH measuring device in the bioreactor. This may be beneficial as the risk of infecting the bioreactor with unwanted microbes in the process of sampling is reduced and no offset effects are caused by the sampling process.

According to embodiments, the second and first CO2 concentrations of the off gas of the respective bioreactors and the total gas influx rate are used for calculating a second CO2 off gas rate for the second bioreactor and for calculating a first CO2 off gas rate of the first bioreactor. Then, the second and first CO2 off gas rates are compared instead of the second and first CO2 concentrations. This approach may be applied in case the total off gas rates in the second and first bioreactor are identical. Some CO2 off gas analyzers may measure a CO2 off gas rate instead of a CO2 concentration and return a CO2 off gas rate to the comparison unit. Provided that the total off gas rate of the two compared bioreactors is identical, the CO2 off gas rate ("ACO") of the two bioreactors may be compared instead of the two CO2 values and a pH meter offset or calibration difference is detected if—given identical total off gas rates and identical measured pH values the measured CO2 off gas rates of the two bioreactors differ.

According to embodiments, the method is used for determining if the first pH measuring device is calibrated differently than the second pH measuring device. The first pH measuring device is at least partially surrounded by the medium within the first bioreactor. For example, the first pH measuring device may be a pH measuring device immersed in the medium of the first bioreactor. The first bioreactor lacks means for manually or automatically taking a sample of the medium in the first bioreactor.

This may have the benefit of allowing using a bioreactor type that prevents a contamination of the medium and/or the generation of offset effects by taking samples for the purpose of measuring the pH value as an offline measurement.

According to other embodiments, the first bioreactor comprises means for manually or automatically taking a sample of the medium in the first bioreactor. Said means may consist, for example, of an opening for taking medium samples from the bioreactor manually, or may consist of robotic arms or drains for automatically or semi-automatically drawing a sample. The method further comprises: during a time interval after filling the medium in the first bioreactor and before adding the cell culture to the medium in the first bioreactor, keeping all openings of the sampling means closed. This may prohibit contamination of the medium in the bioreactor. As the method uses a first pH measuring device residing inside the bioreactor in combination with a CO2 concentration of the gas volume above the medium that can easily be measured without taking samples, embodiments of the invention allow for detecting calibration differences without taking a sample of the bioreactor and thus without risking an infection.

According to embodiments, the method is used for determining if the first pH measuring device is calibrated differently than the second pH measuring device. The determination if the second and first pH measuring device are calibrated differently is performed while the first pH measuring device is at least partially surrounded with the medium in the first bioreactor (thus, by a pH measuring device completely or at least partially located inside the bioreactor) and without taking a sample of the medium of the first bioreactor for performing said determination.

According to embodiments, the determination is performed by using the second and first CO2 concentrations and the second and first pH values as the only data input for said determination. This may be advantageous as said parameter values can easily be obtained by performing online pH value and CO2 concentration measurements.

According to embodiments, the method further comprises performing an online-measurement with the first pH measuring device for measuring the first pH-value, the first pH measuring device being at least partially surrounded with the medium in the first bioreactor.

In addition or alternatively, the method comprises performing an online-measurement by a first CO2 sensor in the off gas of the first bioreactor for providing the first CO2 concentration.

This method may in particular be used determining if the first pH measuring device is calibrated differently than the second pH measuring device (as the first pH measuring device is capable of performing online-measurements, there is typically no offset effect and any deviation from the result of the second pH measuring device are caused by calibration differences or, in case the second pH measuring device is an offline-measuring device, by offset effects of the second pH measuring device.

In many currently used bioreactor types, respective $CO_2$ concentration and pH measuring devices are already present and may easily be employed not only for bioreactor state monitoring and control purposes but also for the purpose of identifying calibration differences and offset effects. It is neither necessary to draw medium samples for pH measurement nor to withdraw or reintroduce the pH measurement device from or into a bioreactor. Thus, the risk of infecting the bioreactor with undesired microbes is reduced. The method may allow identifying calibration differences of two pH-meters of two bioreactors without taking samples from the medium from any one of the two bioreactors.

Using a $CO_2$ sensor that measures the $CO_2$ concentration in the off gas of a bioreactor may be advantageous, because $CO_2$ off gas meters ("$CO_2$ off gas analyzers", "$CO_2$ off gas sensors") are non-invasive, do not need a sampling, can be easily obtained in real time and deliver a value, the $CO_2$ concentration in the off gas and/or the $CO_2$ off gas rate. Thus, $CO_2$ off gas analyzers may give immediate response to intended or unintended process changes in a bioreactor (in contrast to e.g. cell densities or cell counts). Further, off gas analyzers can be calibrated anytime and do not have to be autoclaved.

According embodiments, the method comprises performing an online-measurement with the second pH measuring device for measuring the second pH-value. The second pH measuring device is at least partially surrounded with the medium in the second bioreactor. In addition, or alternatively, the method comprises performing an online-measurement by a second $CO_2$ sensor in the off gas of the second bioreactor for providing the second $CO_2$ concentration. This may have the advantage that also the pH and $CO_2$ concentration values of the second (or "reference") bioreactor may be gathered by means of online measurements, e.g. by means of an immersed, continuous pH-meter, thereby avoiding pH offset effects and reducing the risk of infections caused by the sampling process.

According to embodiments, the method is used for determining if the first pH measuring device outputs a different pH value than the second pH measuring device due to offset effects of a sampling process performed for measuring the first pH value in a sample of the medium of the first bioreactor. The method further comprises performing an offline-measurement with the first pH measuring device for measuring the first pH-value. The first pH measuring device is outside of the first bioreactor and is at least partially surrounded with the medium in a medium sample of the first bioreactor.

Said features may be beneficial if a bioreactor type is used that is technically equipped with offline measurement devices, in particular offline pH measuring devices. In this context, any offset effect determined by a comparison of the second and first pH values and second and first $CO_2$ concentrations may be used for outputting a warning and/or modifying the output of the first pH measuring device in a way that the offset effect caused by the sampling process is compensated.

According to embodiments, the method comprises determining that the second and first pH measuring devices are calibrated differently or determining that the second and first pH measuring devices output different pH values due to offset effects of a sampling process in case one of the following situations occurs:

the second and first $CO_2$ concentrations are identical and the second and first pH values differ from each other by more than a threshold value; or the second and first pH values are identical and the second and first $CO_2$ concentrations differ from each other by more than a further threshold value; or a second data value differs from a first data value by more than a further threshold, the second data value being derived from the second pH value and the second $CO_2$ concentration, the first data value being derived from the first pH value and the first $CO_2$ concentration. For example, in case the total off gas rates are identical for two bioreactors whose pH measuring devices shall be calibrated to allow a comparison of the pH value in the media in both bioreactors, the $CO_2$ off gas rates may be compared instead of the $CO_2$ concentrations.

According to embodiments, in case neither the pH value nor the $CO_2$ concentrations are identical, a control unit of a bioreactor monitoring and/or control system may modify the $CO_2$ gas influx rate. Thereby, both the $CO_2$ concentration in the gas phase as the pH value in the medium may be affected. As soon as either the first pH value is identical to the second pH value or the first $CO_2$ concentration is identical to the second $CO_2$ concentration, the above described determination is performed.

According to embodiments, the method further comprises observing that the second and first $CO_2$ concentration are identical and calibrating the first pH measuring device in a way that the first pH measuring device indicates the same pH value as the second pH measuring device.

For example, in case the second and first $CO_2$ concentrations are identical and the second and first pH value differ from each other by an amount "delta", said "delta" pH offset value can be added to each pH value measured by the first pH measuring device in the future (i.e. at a time later than the first time). The resulting pH values output by the first pH-measuring device thus compensate for the pH offset caused by a sampling process for measuring the second or first pH value and/or compensate for any calibration differences between the second and first pH measuring devices.

According to embodiments, a control unit of a system configured for monitoring and/or minimizing deviations of a state of the first bioreactor from the state of the second bioreactor uses pH values of the first pH measuring device as an input. The minimization of the state differences and/or the comparison of the states of the two bioreactors is performed by the comparison unit analyzing at least said input parameters. The comparison unit may be a software, firmware and/or hardware-implemented piece of program logic, e.g. an application program running on an electronic data processing system. According to embodiments, the comparison unit is operatively coupled to the control unit. For example, the comparison unit may be an integral part of the control unit or may be an application program configured to interoperate with the control unit. The control unit and the monitoring unit may be hosted on the same or on different electronic data processing machines.

This may be advantageous as the use of a first pH measuring device that is calibrated differently than the second pH measuring device and/or whose pH values have an offset effect due to the sampling process can be avoided.

According to embodiments, the receiving of the second and first pH value, the receiving of the second and first $CO_2$ concentration and the comparison of said pH and $CO_2$ concentration values is performed by the comparison unit. In case of determining that the second and first pH measuring devices are calibrated differently, the comparison unit may perform one or more of the following steps:
outputting a warning message;
automatically performing or triggering the performing of a recalibration of the first pH measuring device;
automatically performing or triggering the performing of a replacement of the first pH measuring device by a new first pH measuring device.

Thus, an operator or an automated component of the first bioreactor is enabled to take appropriate actions, e.g. exchange or recalibrate the first pH measuring device and delay the inoculation of the first bioreactor until the problem is fixed.

The comparison unit may be, for example, provided by or executed on an electronic data processing apparatus or part thereof. The apparatus comprises a processor, memory and electronic instructions stored thereon. Upon processing the instructions by the processor, the method of embodiments of the invention is performed by the comparison unit. In some embodiments, the comparison unit is operatively coupled to one or more bioreactor monitoring and/or control application programs. The comparison unit may be an integral part of a system comprising the first and optionally also the second bioreactor. The system, according to some embodiments, comprises further bioreactors whose state shall be monitored and compared with the state of the second bioreactor.

According to embodiments, the comparison unit reads a medium-specific relation from a data storage medium. The medium-specific relation is specific for the medium in the second and in the first bioreactors and indicates a relation between the pH value of the medium and a respective fraction of CO2 gas in a gas volume when said medium is in pH-CO2 equilibrium state with said gas volume and lacks a cell culture. Then, the comparison unit uses the first CO2 concentration as input for the medium specific relation for calculating an absolute pH value expected for the medium in the first bioreactor in pH-CO2 equilibrium at the predefined temperature and pressure and under the absence of a cell culture, Then, the comparison unit (or an operator using the calculation result of the medium specific relation) configures the first pH measuring device such that the calculated absolute pH value is output by said first pH measuring device. For example, the first pH measuring device is calibrated such that in future pH measurements, the first pH measuring device outputs a sum of a measured first pH value and a delta pH, the delta pH being the difference between the measured first pH value and the expected pH value calculated by using the medium specific relation.

The medium-specific relation can be, for example, an equation $PPH_{M1}(CO2)=REL\text{-}M1(CO2)$ obtained by mathematically fitting multiple empirically determined pairs of a pH-value of the medium (M1) and a respectively measured fraction of CO2 gas in a gas volume above said medium. Thereby:
$PPH_{M1}(CO2)$ is the predicted pH value in a medium (M1) when said medium lacks a cell culture and is at pH-CO2 equilibrium with a gas volume above said medium, said gas volume comprising the CO2 concentration used as input parameter;
the CO2 is an input parameter value and represents the CO2 concentration in a gas volume above the medium (M1) in ph-CO2 equilibrium state under the absence of the cell culture;
REL-M1 is a set of one or more parameters connected by operators.

The parameters are obtained e.g. by manually, automatically or semi-automatically performing the following steps:
adjusting samples of the medium M1 lacking the cell culture to multiple different pH values, thereby letting the samples reach pH-CO2 equilibrium with the gas volume above the medium in the respective sample,
determining the fraction of CO2 gas in a in respective gas volume being in ph-CO2 equilibrium with the medium in the samples,
plotting the determined CO2 gas fractions against the respective equilibrium pH values of the samples,
fitting a curve in the plotted values and deriving the parameters of the medium-specific relation from the fitted curve.

Thus, the medium-specific relation may be identified empirically, e.g. before the second or first bioreactor is inoculated with the reference cell culture.

According to some embodiments, the medium specific relation is obtained by filling a bioreactor, e.g. the second bioreactor, with the medium, whereby the medium does not comprise the cell culture cells, and setting the temperature and pressure of the second bioreactor to predefined values, e.g. 20° C. and standard atmospheric pressure. The medium in the bioreactor used for empirically determining the medium-specific relation is referred herein also as one of the samples whose pH value is to be set.

Then, the medium may be set to different pH values by increasing or decreasing the CO2 concentration in the gas volume above the medium via a modified CO2 gas influx rate, and after some time (typically minutes or hours) when the medium has equilibrated (reached pH-CO2 equilibrium state at the given pH and the predefined temperature and pressure), the CO2 concentration in the gas volume above said medium (which correlates with the CO2 partial pressure at said equilibrium state) is measured. Said measuring is performed e.g. by analyzing the CO2 concentration in the gas volume above the medium or via the CO2 volume fraction in the off gas. The acquired pairs of equilibrium pH-values and CO2 concentrations (or CO2 off gas values) measured in the sample (bioreactor or aliquot) are plotted, i.e., represented in a coordinate system. The plotting may be performed automatically by an electronic data processing system which may in addition output the plot in the form of a paper-based printout and/or a plot displayed on a display screen. The plotting may also be performed manually. A curve is fitted automatically or manually to said plot and parameters being descriptive of said fitted curve are computed. The parameters define the medium-specific relation of pH-value and CO2 concentration of a gas volume above said medium when said medium is in pH-CO2 equilibrium at a particular pH value. The pH value is preferably set by adjusting the CO2 influx rate, not by adding basic or acid substances in order to avoid a modification of the composition of the medium.

After having computed the parameters, the medium specific relation may be transferred to the comparison unit, e.g. via a graphical user interface allowing a user to enter the relation manually, via a portable storage medium or via a network connection.

According to other embodiments, the medium-specific relation is obtained by creating multiple samples in the form of aliquots of said medium, each sample having a different pH value. The samples are left at a predefined temperature and pressure for some time to allow pH-CO2 equilibration between the gas and the liquid medium in each sample.

The samples can be obtained sequentially, e.g. by changing the pH value of a single sample and performing sequential measurements, or can be obtained by creating multiple samples of said medium in parallel, each aliquot being set to a different pH value by modifying the CO2 concentration of the gas volume above the medium. The sample can be filled into any container allowing the setting and measuring of a current pH value and allowing the modification of the CO2 concentration and the measuring of a CO2 concentration or CO2 off gas rate at equilibrium state. Preferentially, the pH value in the respective samples is set by adapting the CO2 influx rate and thus the CO2 concentration in the gas phase of a bioreactor in a way that the pH value adapts accordingly. This may be advantageous as a modification of the composition of the medium (except of the dissociation product of solved CO2) does not change when using CO2 rather than acids or bases for adapting the pH.

According to some embodiments, the equation $PPH_{M1}(CO2)=REL-M1(CO2)$ is a linear equation according to $PPH_{M1}(CO2)=a1 \times pH + a2$. In this case, the parameters a1 and a2 are the parameters derived from the fitted curve. The $PPH_{M1}(CO2)$ indicates the predicted pH value in a medium in equilibrium state with a gas volume having the particular CO2 concentration used as input to said equation.

According to other embodiments, the equation $PPH_{M1}(CO2)=REL-M1(CO2)$ is a polynomial equation according to $PPH_{M1}(CO2)=b1 \times pH^2 + b2 \times pH + b3$. In this case, the parameters b1, b2 and b3 are the parameters derived from the fitted curve.

Empirically determining the medium-specific relation and the corresponding medium-specific parameters may have the beneficial effect that even in case the exact composition of the medium is not known (which is commonly the case for many media in the market), the impact of a particular pH value on the equilibrium CO2 concentration in an air volume in pH-CO2 equilibrium with said medium can be determined experimentally. Thus, an absolute pH value can be calculated and can be used for calibrating a pH measuring device also when using media types whose composition is not known.

According to embodiments, the cells of the cell cultures are prokaryotic or eukaryotic cells, in particular mammalian cell culture cells.

According to embodiments, the second bioreactor differs from the first bioreactor in respect to one or more of the following features:
a) the gas volume in the bioreactor,
b) the medium volume in the bioreactor,
c) the Reynolds number of the bioreactor,
d) the Newton number of the bioreactor,
e) the dimensions of the bioreactor,
f) geometrical features of the bioreactor and/or bioreactor baffles,
g) the stirrer configuration,
h) the stirring rate,
i) the volumetric mass transfer coefficient for oxygen (kLa) of the bioreactor,
j) total gas influx rate and/or O2 influx rate and/or N2 influx rate and/or CO2 influx rate,
k) power input,
l) pressure in the bioreactor,
m) gas bubble hold time in the medium,
n) gas bubble size and distribution in the medium,
o) surface speed,
p) a parameter calculated as a derivative from one or more of the parameters a)-o);
q) the geographic location of the two bioreactors (e.g. different countries, cities, buildings)

The "power input" parameter as used herein specifies the amount of power input of a stirrer of a bioreactor. Different stirrer configurations can have different power inputs at identical agitation or identical tip speeds. Power input at identical stirrer speeds may depend on the viscosity of the medium.

By comparing CO2 off gas concentrations, the calibration state of pH measuring devices of two bioreactors can be easily compared: identical CO2 concentrations in the off gas indicate identical calibration of pH measuring devices of different bioreactors even in case said bioreactors have different Reynolds and/or Newton numbers, have a different speed or configuration of the stirrer or the like.

According to embodiments, the comparison unit receives a third CO2 concentration and a third pH value. The third CO2 concentration is a CO2 concentration of a third gas volume above the medium in the second bioreactor. The third CO2 concentration and the third pH value are measured at a third time. The third time is a time when the medium in the second bioreactor is in pH-CO2 equilibrium state at a predefined temperature and pressure with the third gas volume and after said equilibrium state is modified by the metabolism of the cell culture in the second bioreactor. The third pH value is a measured value provided by the second pH measuring device.

Then, the comparison unit receives a fourth CO2 concentration and a fourth pH value. The fourth CO2 concentration is a CO2 concentration of a fourth gas volume above the medium in the first bioreactor. The fourth CO2 concentration and the fourth pH value are measured at a fourth time. The fourth time is a time when the medium in the first bioreactor is in pH-CO2 equilibrium state at the predefined temperature and pressure with the first gas volume and after said equilibrium state is modified by the metabolism of the cell culture in the first bioreactor. For example, after some hours or even days, some cells start excreting substances, e.g. lactate, into the medium which change the pH and/or composition of the medium. The fourth pH value is a measured value provided by the first pH measuring device. The lapsed time between the third time and the inoculation of the second bioreactor is identical to the lapsed time between the fourth time and the inoculation of the first bioreactor.

In addition, the comparison unit receives a measured second oxygen uptake rate of the cell culture in the second bioreactor at the third time and receives a measured first oxygen uptake rate of the cell culture in the first bioreactor at the fourth time.

In case the second and first oxygen uptake rates are identical, the comparison unit compares the third and fourth pH values and compares the third and fourth CO2 concentrations for determining if the second and first pH measuring devices are calibrated differently or for determining if the second and first pH measuring devices output different pH values due to offset effects of a sampling process performed for measuring the third or fourth pH value in a sample of the medium of a respective one of the second and first bioreactors.

The second and first pH measuring devices are determined to be calibrated differently or are determined to output different pH values due to offset effects of a sampling process in case one of the following situations occurs:
the third and fourth CO2 concentrations are identical and the third and fourth pH values differ from each other by more than a threshold value; or
the third and fourth pH values are identical and the third and fourth CO2 concentrations differ from each other by more than a further threshold value Embodiments of the invention assume that in case the temperature and pressure is identical in the second and first bioreactor and in case in addition the oxygen uptake rate is identical, then differences in the measured pH values result from calibration errors or offset effects of a sampling process for measuring a pH value.

Said features may be particularly advantageous as they allow to determine if two pH measuring devices are calibrated differently or show sampling offset effects even in case the metabolism of the cells has started modifying the pH-CO2 equilibrium state of a bioreactor, e.g. by excreting lactate (and without taking samples for offline pH measurements). It was observed that often the oxygen uptake rate of cells correlates with the state of a particular cell culture, so in case the OUR of the cell cultures in two bioreactors is identical and also the CO2 concentrations in the off gas, temperature and pressure are identical, any observed pH differences are caused by calibration errors or sampling-based offset effects.

In a further aspect, the invention relates to a comparison unit configured for:
  receiving a second CO2 concentration and a second pH value, the second CO2 concentration being a CO2 concentration of a second gas volume above a medium in the second bioreactor, the second CO2 concentration and the second pH value being measured at a second time, the second time being a time when the medium in the second bioreactor is in pH-CO2 equilibrium state at a predefined temperature and pressure with the second gas volume and before said equilibrium state is modified by the metabolism of a cell culture in the second bioreactor, the second pH value being a measured value provided by a second pH measuring device operatively coupled to a second bioreactor;
  receiving a first CO2 concentration and a first pH value, the first CO2 concentration being a CO2 concentration of a first gas volume above a medium in the first bioreactor, the first CO2 concentration and the first pH value being measured at a first time, the first time being a time when the medium in the first bioreactor is in pH-CO2 equilibrium state at the predefined temperature and pressure with the first gas volume and before said equilibrium state is modified by the metabolism of a cell culture in the first bioreactor, the first pH value being a measured value provided by a first pH measuring device operatively coupled to a first bioreactor;
  comparing the second and first pH values and CO2 concentrations for determining if the second and first pH measuring devices are calibrated differently or for determining if the second and first pH measuring devices output different pH values due to offset effects of a sampling process performed for measuring the second or first pH value in a sample of the medium of a respective one of the second and first bioreactors.

In a further aspect the invention relates to a system configured for monitoring and/or minimizing deviations of a state of the first bioreactor from the state of the second bioreactor. The system comprises a control unit for monitoring and/or controlling at least the first and optionally also the second and one or more further bioreactors and comprises a comparison unit according to any one of the embodiments described herein. The system further comprises at least the first bioreactor and the first pH measuring device. The control unit is configured to monitor and/or control a state of a cell culture at least in the first bioreactor, thereby using pH values repeatedly measured by the first pH measuring device.

According to embodiments, the system further comprises the second bioreactor, whereby second and first bioreactors are located in different geographic regions and optionally coupled to the comparison unit via a network, e.g. the internet, for communicating the CO2 concentrations and pH values.

According to embodiments, the second time is a time before the second bioreactor is inoculated with a cell culture. The second time may also be a time at or after inoculation of the second bioreactor with the cell culture and before the metabolism of said cell culture modifies the pH value of the medium in the second bioreactor.

The first time is a time before the first bioreactor is inoculated with a cell culture. Alternatively, the first time is a time at or after inoculation of the first bioreactor with the cell culture and before the metabolism of said cell culture modifies the pH value of the medium in the first bioreactor.

A "profile" as used herein is a representation of the variation in a parameter value versus time.

A "tank" as used herein is a container for holding, transporting, or storing liquids. A tank can be, for example, a bioreactor or a harvest or transport tank comprising the medium, cell culture and reaction products of a bioreactor. A tank may also be a calibration box that is filled with cell-free medium and is used for calibrating a pH measuring device.

A "calibration box" as used herein is a tank with a known medium, whereby the tank is operatively coupled to a CO2 sensor and is configured for temporarily housing one or more pH measuring devices for calibrating the pH measuring devices using the CO2 offgas concentration measured by the sensor. For example, the calibration box can be a bioreactor that is currently not used for growing a cell culture but is used solely or predominantly for calibrating pH measuring devices. Alternatively, the calibration box may be a special purpose container, in particular a portable container that can be carried by a person to different places for calibrating the pH meters in different laboratories. The calibration box comprises a medium with known properties (current temperature, pressure, known medium specific relation or known composition in the case of purely bicarbonate-buffered media) and comprises a CO2 sensor in the gas volume above the medium or in the offgas of the calibration box. It further comprises an opening for easily inserting and removing a pH measuring device and may comprise one or more fixing devices for temporarily fixing the one or more pH measuring devices in the calibration box such that they are at least partially surrounded by the medium in the calibration box.

A "predefined" temperature and pressure as used herein specifies to a temperature and pressure that is controlled or at least known by an operator of the first and/or second tank or that is controlled by or at least "known" by a program logic configured to operate the first and/or second tank or the pH measuring devices contained therein. Thus, the "predefined" temperature and pressure may also be referred to as "given" temperature and pressure. It may be necessary to ensure that the first and second pH values and first and second CO2 values are measured at the same, given temperature and pressure.

A "comparison unit" as used herein is a piece of program logic, e.g. an application program or module, a computer chip or another piece of hardware or firmware that is configured for receiving and processing one or more measured pH values and one or more measured CO2 concentrations in the off gas of a tank for determining if a pH measuring error occurred. For example, the comparison unit may be a program module that is part of or interoperates with a calibration software or bioreactor monitoring or control software.

A pH measuring device being "operatively coupled" to a tank can be, for example, a pH measuring device that is permanently or temporarily located within the tank and is configured to perform on-line pH measurements.

A "bioreactor" as used herein is a vessel in which a chemical process is carried out which involves organisms or biochemically active substances derived from such organisms. This process can be, for example, aerobic or anaerobic. A plurality of different bioreactor types exist which vary in shape (e.g. cylindrical or other), size (e.g., milliliters, liters to cubic meters) and material (stainless steel, glass, plastic, etc.). According to embodiments, the bioreactor is adapted for growing cells or tissue in cell cultures. Depending on the embodiment and/or on the mode of operation, a bioreactor may be a batch bioreactor, fed batch bioreactor or continuous bioreactor (e.g. a continuous stirred-tank reactor model). An example of a continuous bioreactor is the chemostat.

An "Online-measurement" as used herein is a process of obtaining a measurement value being descriptive of state features of a bioreactor or of a cell culture contained therein, whereby the duration required for performing the measurement is shorter than the time during which said features significantly change. A significant change can be a change by more than a predefined threshold value. For example, a change by more than 5% may be considered as a significant change. The threshold may vary for different features. Online-measurements may allow controlling a bioreactor in real time.

An "Offline-measurement" is a process of obtaining a measurement value being descriptive of state features of a bioreactor or of a cell culture contained therein, whereby the duration required for performing the measurement is longer than the time during which said features can significantly change. A significant change can be a change by more than a predefined threshold value. A typical example for an offline-measurement is the automated, semi-automated or manual sampling of a the medium e.g. for measuring a current pH value. Offline measurements are based on a discontinuous sampling process. As the bioreactor features may meanwhile have changed since the sample was taken, controlling the bioreactor based on offline-measurement data tends to be of low quality due to significant latency times between the moment of measurement and the moment of performing a respective control operation.

A significant change can be a change by more than a predefined threshold value, for example 2% or any other percentage value, depending on the respective state feature. A typical example for an offline-measurement is the automated, semi-automated or manual sampling of a probe of the medium e.g. for measuring a current pH value for calibrating a pH measuring device when initiating a bioreactor.

A discontinuous sampling process for obtaining the measurement value from a sample may have the disadvantage that the bioreactor features may meanwhile have changed. Thus, controlling the bioreactor based on offline-measurement data tends to be of low quality due to significant latency times between the moment of measurement and the moment of performing a respective control operation.

A "pH measuring device" or "pH meter" as used herein is a device and/or substance used for measuring a current pH value in a medium. A pH meter can be, for example, a pH indicator (like phenolphthalein)—in form of a solution or pH strips—or a potentiometric apparatus. According to preferred embodiments, the pH meter is a continuous pH meter, i.e., a pH meter capable of continuously and repeatedly measuring the pH of the medium of a bioreactor without having to draw samples and without having to insert said pH meter in the medium for each individual measurement. For example, a pH meter can be a precise voltmeter, connected to the medium and to a reference electrode, and scaled in such a way that it displays not the measured potential, but ready pH value. Preferentially, the pH meter is immersed in the medium and is used for repeatedly measuring the current pH value in the medium during the whole time while cultivating cells in the bioreactor. For example, the pH meter may measure a current pH value every minute, or every 30 minutes, or every hour. In typical today's pH meter reference electrode is built into the pH electrode, which makes the device compact.

A "$CO_2$ measuring device", "$CO_2$ sensor", "$CO_2$ meter" or "$CO_2$ analyzer" as used herein is a device used for measuring a current $CO_2$ concentration in a gas volume, e.g. the gas volume above the medium of a bioreactor or the off gas of a bioreactor.

According to embodiments, the current $CO_2$ concentration of the second and/or first bioreactor is measured by a continuous $CO_2$ off gas meter, i.e., a device capable of measuring the current $CO_2$ concentration in the off gas of a bioreactor repeatedly without having to insert or replace a hardware module into the bioreactor or its connected off gas pipe or pipes for each $CO_2$ concentration measurement. Using continuous pH measuring devices and/or continuous $CO_2$ off gas meters may be advantageous as the respective measurements can be performed easily and repeatedly without causing offset effects and/or without the need to take a sample of the medium. Many existing bioreactors already comprise one or more immersed pH-meters and/or comprise or are coupled with measurement devices capable of measuring the $CO_2$ concentration and/or the $CO_2$ off gas rate.

Depending on the embodiment, the bioreactor (or reference bioreactor) comprises a single gas inflow line or pipe or multiple gas inflow lines or pipes. For example, a single gas inflow line or pipe may be used for delivering environmental air or (already expanded) compressed air from special suppliers into the bioreactor (reference bioreactor). Said environmental air or compressed air may consist of a mixture of gasses, in particular N2, O2 and CO2 that is typical for the earth's atmosphere or has a different composition. In addition or alternatively, the single gas inflow line or pipe or any of the other gas inflow lines or pipes may be used for delivering individual gases such as N2, O2 and CO2 to the bioreactor, e.g. to control the cell growth.

According to embodiments, one or each of the two bioreactors respectively comprises a microsparger for generating very finely dispersed gas bubbles from the inflowing gas for accelerating the establishment of a pH-CO2 equilibrium between the medium and the gas volume in the bioreactor. For example, a microsparger may be used for an influx gas mix or for each individual influx gas component separately. In addition, or alternatively, one or each of the two bioreactors is configured and operated such that the carbon dioxide and one or more other gases (e.g. nitrogen, oxygen and/or air) are added together simultaneously to the bioreactor as a gas mix. For example, all influx gases may be input to the bioreactor as gas mix, e.g. via a submersed pipe opening or a microsparger.

Preferentially, all process gases are input to the bioreactor via a microsparger and/or in the form of a gas mix in case the volume of the bioreactor is below a threshold volume of e.g. 400 liter or e.g. 200 liter.

According to embodiments, the aeration rate and bubble size of the influx gases in the medium of the bioreactor is chosen such that all gas bubbles reach pH-CO2 equilibrium with the medium before leaving the bioreactor or are dissolved completely in the medium.

Said features may be advantageous as they ensure that the gas bubbles reach equilibrium state before their gas content leaves the bioreactor: a microsparger generates very finely dispersed gas bubbles of the inflowing gas, thereby accelerating the establishment of a pH-CO2 equilibrium between the medium and the gas volume in the bioreactor. Inputting the CO2 gas as a gas mix avoids the situation that the CO2 transition rate from a pure CO2 gas bubble into the medium is larger than the CO2 transition rate from the medium to e.g. air or N2 bubbles (the transition rate may depend on the amount of CO2 concentration difference between medium and different types of bubbles). Thus, said measures ensure the comparability of the state of bioreactors over a wide range of bioreactor volumes, including volumes below e.g. 400 liter.

A "profile" as used herein is a representation of the variation in a parameter value versus time.

The "pH-CO2 equilibrium" indicates a state of a system comprising an aqueous solution (e.g. a cell culture medium) and an air volume above said solution (e.g. the gas volume in a bioreactor) whose pH value and CO2 partial pressure are in chemical equilibrium according to the Henderson-Hasselbalch equation. The CO2 partial pressure corresponds to the fraction of CO2 gas in the total gas volume above the medium. The Henderson-Hasselbalch equation describes the relationship of pH as a measure of acidity with the acid dissociation constant (pKa), in biological and chemical systems. If a gas comprising $CO_2$ is in contact with an aqueous liquid, e.g. a culture medium, at least a small fraction of the CO2 dissolves in said liquid. At room temperature, for example, the solubility of carbon dioxide is about 90 cm$^3$ of $CO_2$ per 100 ml water ($c_l/c_g=0.8$). Any water-soluble gas becomes more soluble as the temperature decreases. A small fraction (ca. 0.2-1%) of the dissolved $CO_2$ is converted to $H_2CO_3$. Most of the $CO_2$ remains as solvated molecular $CO_2$. This process can be described by the following formulas:

Carbonic acid (H2CO3) equilibrium:

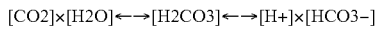

[H+]×[HCO3−]=K×[CO2]×[H2O], wherein K=equilibrium constant

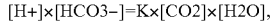

A "CO2 volume fraction" as used herein is the fraction of CO2 gas in a total gas volume. The unit may be, for example, Vol. %. It is also referred to as "CO2 concentration" of a gas volume, the concentration being specified in Vol. %.

A "medium" or "cell culture medium" is a liquid or gel designed to support the cultivation and typically the growth of microorganisms or cells, or small plants like the moss Physcomitrella. There are different media for growing different types of cells. Typically, a medium is a water-based solution comprising mixture of one or more substances such as salt(s), carbohydrates, trace elements, peptides and/or proteins. There exist a plurality of different media on the market, e.g. for cell culture of specific cell types derived from plants or animals, and microbiological culture for growing microorganisms, such as bacteria or yeast. A medium may be, for example, a nutrient medium, e.g. an LB medium (Lysogeny Broth), a minimal medium, a selective medium, a differential medium, or an enriched medium. Some media may require a CO2 environment of e.g. 5-10% CO2 to maintain physiological pH.

According to some embodiments, the expression "two media being the same" implies that the two media (e.g. the medium in the reference bioreactor on the one hand and the medium in the monitored and/or controlled bioreactor on the other hand) comprise—given a particular pressure, temperature and CO2 concentration in the gas volume above said medium—the same composition and concentration of organic and inorganic compounds and solvents and/or have been manufactured using the same manufacturing protocols and conditions within the context of measuring accuracy.

According to some embodiments, said expression implies that the two media can differ in respect to any of said criteria (composition, concentration, manufacturing protocol) only in so far as said difference (at a given temperature, pressure and CO2 concentration in the gas volume above said medium) has no or approximately no impact on the pH-CO2 equilibrium of said medium at a plurality of different pH values and in so far as the medium-specific relations derived empirically from said two media respectively are identical.

To "cultivate a cell culture" as used herein typically means that the cells culture is grown, i.e., the number of the cells of the cell culture increases. In some occasions, however, the number of cells may also stagnate or even decline.

In the following embodiments of the invention are explained in greater detail, by way of example only, making reference to the drawings in which.

DETAILED DESCRIPTION

Figure 1:
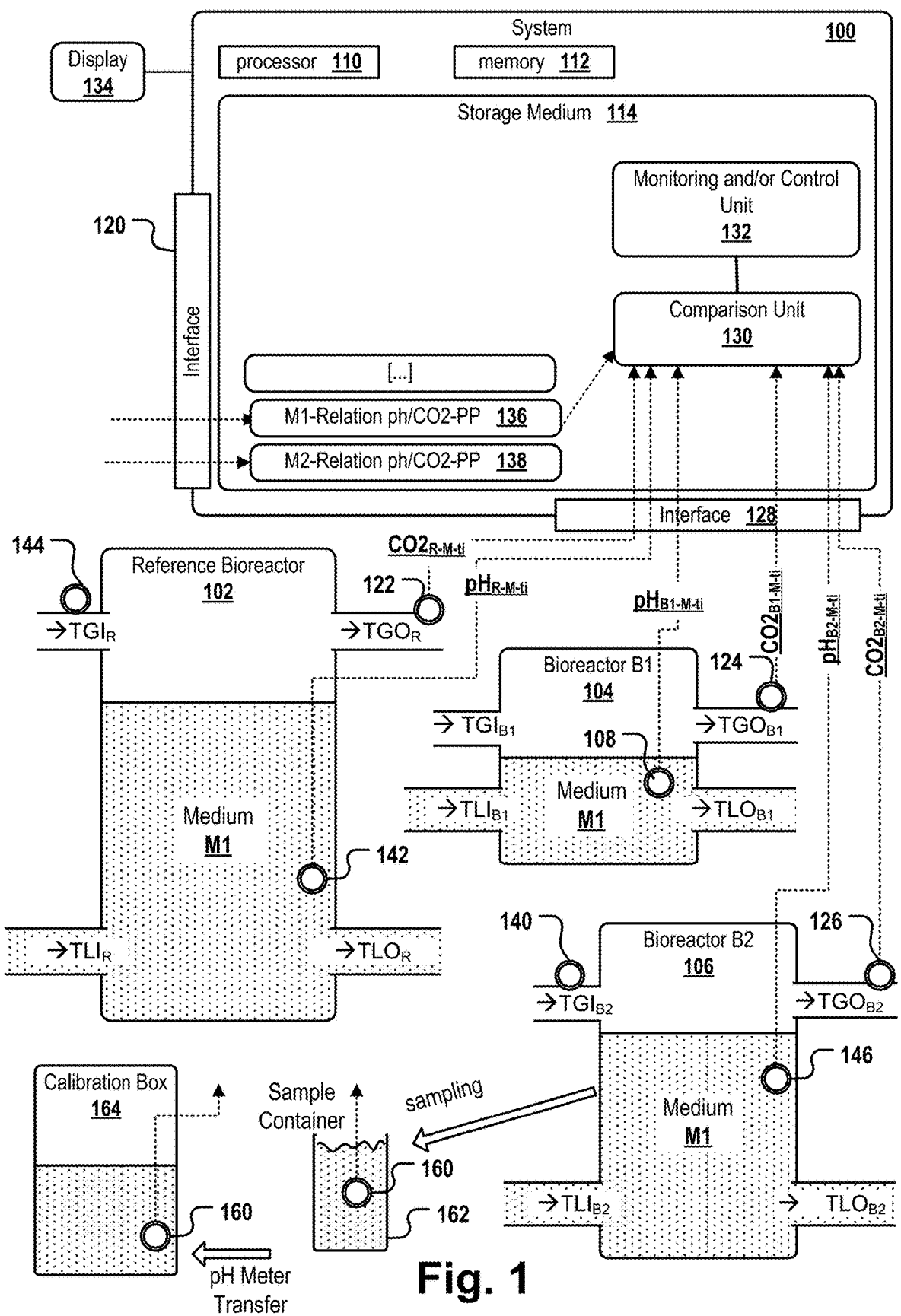
FIG. 1 shows a block diagram of a system for monitoring and/or controlling one or more bioreactors configured to detect a pH measuring device calibration deviation or a pH measurement offset effect.
Figure 2:
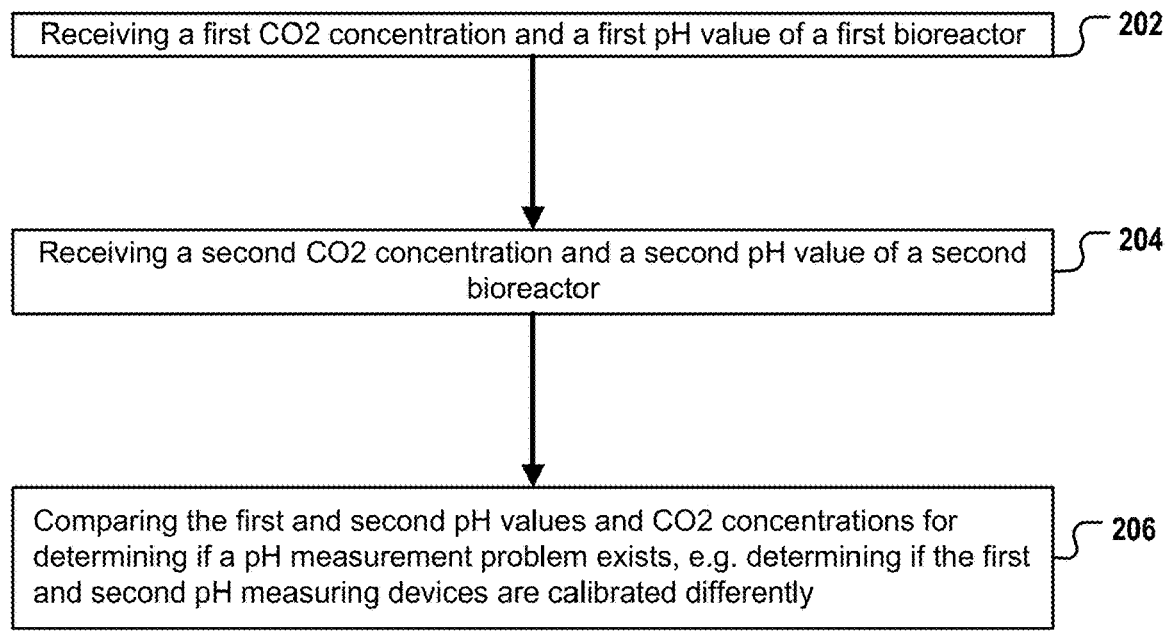
FIG. 2 shows a flowchart of methods for detecting pH measuring device calibration deviations or pH measurement offset effects.

FIG. 1 shows a block diagram of a system 100 comprising a control unit 132 for monitoring and/or controlling one or more bioreactors. The system 100 comprises a comparison unit 130 for comparing measured pH values and CO2 concentrations received via an interface 128 from two or more bioreactors. In the following, embodiments of the invention will be described by making reference to a corresponding method for identifying calibration differences and pH measurement sampling offset effects as indicated in the flow chart of FIG. 2

FIG. 1 shows a system 100 allowing for real-time and accurate comparison of pH values measured by pH measuring devices of two or more bioreactors and of CO2 concentrations measured by off gas analyzers of respective bioreactors for identifying calibration differences and offset effects in two compared bioreactors immediately, without having to take medium samples of one of the bioreactors and without the need to use a "standard" solution of a known pH value for determining calibration errors or offset effects.

The system 100 comprises a processor 110, a main memory 112 and a non-transitory storage medium 114. The storage medium comprises computer readable instructions which, when executed by the processor 110 cause the processor to perform a method for automatically monitoring and/or controlling one or more bioreactors 102, 104, 106 as described for embodiments of the invention.

The storage medium 114 comprises at least one data structure 136, e.g. a file or a database record, being indicative of a pH-CO2-concentration relation that is particular for the medium M1 contained in any of the bioreactors 102, 104, 106.

In addition, the storage medium may comprise medium-specific relations 138 of other cell culture media M2. The medium-specific relations 136, 138 may be received via a data communication interface 120, e.g. a network interface, an USB-port, a CDROM drive or the like.

The system 100 may further comprise an interface 126 for dynamically receiving current measurement values from one or more monitored and/or controlled bioreactors 102, 104, 106. The interface 126 may also be a network interface, e.g. the Internet, or an Intranet. The measurement values are in particular a current pH value and a current CO2 concentration measured in the off gas of the respective bioreactor. A comparison unit 130 uses the received measurement values received from the monitored and/or controlled bioreactors 102, 104, 106 for determining if the respective pH measuring devices are calibrated in the same way and are free of offset effects which prohibit a correct comparison of measured pH values received from different bioreactors. Optionally, the comparison unit 130 also uses the medium-specific relation 136 of the medium M1 as input in order to determine if a pH measuring device outputs a correct absolute pH value.

The first bioreactor 104 is initialized by filling the first bioreactor with the cell-free medium M1 and by starting continuously adding gas, e.g. by transporting environmental air and/or its individual components (N2, O2 and/or CO2) to the bioreactor and optionally also by starting continuously adding liquids (the cell-free medium, optionally additional liquids such as feed, etc.). In addition, the stirrers may be started. The first bioreactor thereby is operated at a temperature and pressure that is identical to the temperature and pressure used for initiating the second bioreactor.

After some time (typically minutes or hours), the medium in the first bioreactor and the air volume in the first bioreactor above the medium will have reached pH-CO2 equilibrium state and the first pH and CO2 concentration values are measured in the medium and off gas of the first bioreactor. In order to set the medium in the first bioreactor to a particular pH value, the CO2 influx rate to the first bioreactor may be modified accordingly, because the CO2 concentration in the gas volume has an impact on the pH value of the medium.

In a second step 202, the comparison unit 130 receives a second CO2 concentration CO2-R-M-ti and a second pH value $pH_{R-M-ti}$. The second CO2 concentration is a CO2 concentration of a second gas volume above a medium in a second bioreactor 102. The second CO2 concentration and the second pH value being measured at a second time ti. The second time is a time when the medium in the second bioreactor is in pH-CO2 equilibrium state at a predefined temperature and pressure (e.g. 20° C. and normal atmospheric pressure) with the second gas volume and before said equilibrium state is modified by the metabolism of a cell culture in the second bioreactor. For example, the second time ti is a time before the bioreactor 102 is inoculated with the cell culture or a time shortly after the inoculation so the metabolism of the cells does not have an impact on the pH-CO2 equilibrium in the bioreactor 102 yet. The second pH value is a measured value provided by a second offline or online pH measuring device 142 operatively coupled to the second bioreactor 102. In the depicted example, the second pH measuring device is an online pH meter immersed in the medium M1 of the second bioreactor 102.

In a next step 204, the comparison unit receives a first CO2 concentration $CO2_{B1-M-ti}$ and a first pH value $pH_{B1-M-ti}$. The first CO2 concentration is a CO2 concentration of a first gas volume above a medium in a first bioreactor which may be measured, for example, in the off gas of the first bioreactor 104. The first CO2 concentration and the first pH value are measured at a first time. The first time is a time when the medium in the first bioreactor 104 is in pH-CO2 equilibrium state at the predefined temperature and pressure with the first gas volume and before said equilibrium state is modified by the metabolism of a cell culture in the first bioreactor.

For example, a CO2 analyzer device 122, also referred to as "carbon dioxide sensor" may be used for repeatedly measuring the concentration of CO2 in the off gas. Common examples for CO2 sensors are infrared gas sensors (NDIR) and chemical gas sensors. NDIR sensors are spectroscopic sensors to detect CO2 in a gaseous environment by its characteristic absorption. Alternatively, the CO2 sensor may be a microelectromechanical sensor.

The first pH value is a measured value provided by a first pH measuring device 108 operatively coupled to the first bioreactor 104. The medium in the second and in the first bioreactor are the same.

In some embodiments, the second bioreactor 102, also referred to as "reference bioreactor", is used for growing a cell culture days, weeks or even years before the first bioreactor 104 is inoculated in order to grow a cell culture under basically the same conditions as in the reference bioreactor before. In this case, the second and first time may lie years apart, but respectively represent a time at which the respective bioreactor is initialized and does not (yet) comprise a cell culture having an impact on the pH-CO2 equilibrium. In this case, the second pH value and the second CO2 concentration are measured before the first pH value and first CO2 concentration is measured. In other embodiments, the second and the first bioreactors are operated in parallel and the second and first pH and CO2 values may be measured and received by the comparison unit approximately at the same time.

In step 206, the comparison unit compares the second and first pH values and CO2 concentrations for determining if the second and first pH measuring devices are calibrated differently.

The comparison unit will determine that the second and first pH measuring devices are calibrated differently or that at least one of said devices is affected by an offset effect (caused by the sampling procedure) in case:

the second and first $CO_2$ concentrations are identical and the second and first pH values differ from each other by more than a threshold value; or the second and first pH values are identical and the second and first $CO_2$ concentrations differ from each other by more than a further threshold value In case the second and the first pH measurement devices are both online measuring devices, there do not exist any offset effects caused by a sampling process. In this case, the comparison unit determines that there is a calibration difference between the second and the first pH measuring device and may output a warning message and/or a delta of the second and first pH values on the display 134. The display device may be e.g. a computer monitor or a monitor of a smartphone. Thus, an operator may prohibit inoculation of the first bioreactor and perform a recalibration or an exchange of the first pH measuring device. It is also possible that the moderator or the comparison unit reconfigures the first pH measuring device in a way that it outputs a value being identical to the second pH value for the medium in the first bioreactor whose equilibrium $CO_2$ concentration in the (off)gas phase was determined to be identical to the equilibrium $CO_2$ concentration in the (off)gas phase of the second bioreactor. In some embodiments, the control unit 132 controls one or more parameters of one or more of the bioreactors 102, 104, 106 such that the difference of environmental conditions for the cells in the first bioreactor to the environmental conditions for the cells in the second (reference) bioreactor is minimized. The control unit can be, for example, a software and/or hardware module being operatively coupled to the comparison unit 130 for receiving the results of the comparison. The control unit is capable of controlling the configuration and operation of one or more engineering processes and parameters. For example, the control unit 132 may be operable to increase or decrease the influx of liquids having an impact on the pH value, e.g. may increase or decrease the influx of a citric acid or of a 1 M NaOH solution and/or may increase or decrease $CO_2$ gas influx for modifying the pH value in the medium of a bioreactor.

The medium M1 can be, for example, Kaighn's Modification of Ham's F-12 Medium comprising, for example, putrescine, thymidine, hypoxanthine, zinc, and higher levels of all amino acids and sodium pyruvate. These additions allow the medium to be supplemented with very low levels of serum or defined components, for some cell types. Ham's F-12K (Kaighn's) Medium contains no proteins or growth factors, and is therefore often supplemented with growth factors and Fetal Bovine Serum (FBS) that may be optimized for a particular cell line. Ham's F-12K (Kaighn's) Medium uses a sodium bicarbonate buffer system (2.5 g/L). The medium M2 may be an LB medium, and there may exist reference profiles for a plurality of other media M3, M4, e.g. for cultivating bacteria or plants for a variety of purposes and corresponding "projects".

The system 100 comprises the comparison unit and one or more bioreactors 104 106 which are to be monitored and/or controlled by a control unit 132 operatively coupled to the one or more bioreactors. As can be inferred from FIG. 1, the dimensions and engineering parameters (stirring rate and configuration, bubble size, dimension, medium volume etc.) of the monitored or controlled bioreactors may differ from each other and/or may differ from the respective parameters of the reference bioreactor. The bioreactors 102, 104, 106 may be located at different geographic regions. One or more of the bioreactors send monitoring data (current pH and $CO_2$ concentration in the off gas and/or $CO_2$ off gas rates) to the comparison unit 130 and/or the control unit 132 and optionally also receive control data from the control unit 132 or receive control data for reconfiguring, recalibrating or exchanging a pH measuring device from the comparison unit. The reference bioreactor may but does not have to be coupled to the system 100. It is sufficient that the second pH and $CO_2$ concentration values gathered from the reference bioreactor are accessible by the comparison unit 130 when initiating the first bioreactor (or any further bioreactor 106 whose pH measuring device shall be calibrated in the same way as the second pH measuring device and should be free of any offset effects in respect to the pH values measured by the second pH measuring device 142). The second bioreactor and each of the first bioreactors 104, 106 comprise the same medium M1 and are inoculated with the same type of cell culture.

Preferentially, the monitored and/or controlled bioreactor 104, 106 at least at the time point of initialization is operated under the same temperature and pressure as the reference bioreactor. However, it is possible that while operating the bioreactor 104, 106, the temperature and/or pressure is modified in order to minimize state differences in respect to the cell culture state in the reference bioreactor.

Figure 3:
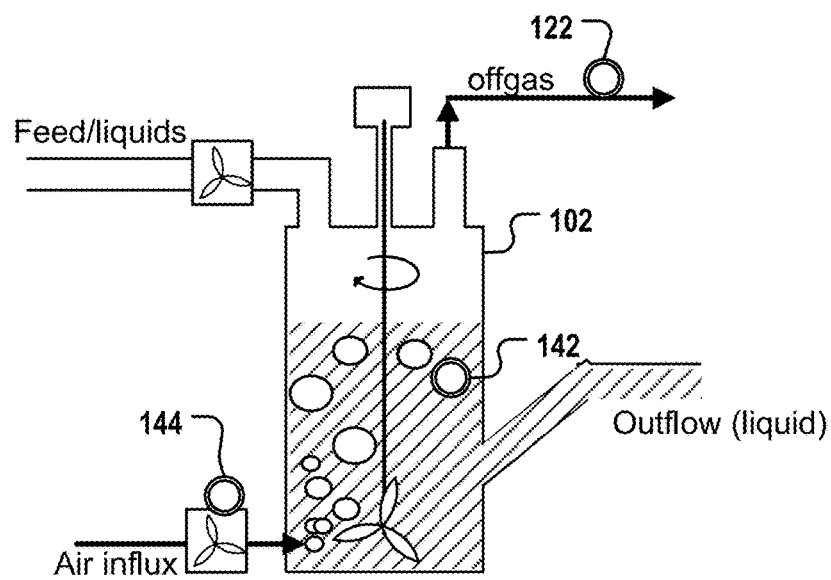
FIG. 3 shows components of a bioreactor.

FIG. 3 shows an embodiment of a bioreactor 102, 104, 106. The bioreactor is coupled to a second pipe or hose for transferring fresh medium and optionally one or more further liquids into the bioreactor. The bioreactor is in addition coupled to an outflow and to one or more first pipes or hoses for transferring gases, e.g. environmental air and/or $N_2$ gas and/or $O_2$ gas and/or $CO_2$ gas into the bioreactor.

In addition, the bioreactor is coupled to a third pipe or hose for the off gas. The first pipe or hose may comprise a sensor 144 for determining a current total gas influx rate. The third pipe or hose may comprise a sensor 122, e.g. a $CO_2$ off gas analyzer, to selectively measure the off gas $CO_2$ concentration and the amount of $CO_2$ gas transferred through the third pipe per time unit. According to other embodiments, there may be not pipes for the influx and outflux of liquids and nutrients may be fed to the bioreactor by means of step-wise bolus addition of a feed solution.

In many bioreactor types, the influx gasses are fed (as a gas mixture or via separate openings) into the bioreactor via one or more submersed gas intakes. In case the bioreactor comprises an additional headspace aeration, the influx rate of said "headspace" influx gas fraction and/or the air circulation of the gas phase above the medium have to be configured such that all gases fed into the bioreactor via headspace aeration reach pH-$CO_2$ equilibrium with the medium of the bioreactor before leaving the bioreactor. Also in case the headspace aeration is the only aeration mechanism of the bioreactor, the influx rate of said "headspace" influx gas fraction has to be configured such that all gases fed into the bioreactor reach pH-$CO_2$ equilibrium with the medium of the bioreactor before leaving the bioreactor.

Alternatively (e.g. in case a pH-$CO_2$ equilibrium of the headspace aeration gases with the medium cannot be reached in time), the additional headspace aeration is turned off before measuring the $CO_2$ concentration in the off gas for performing the pH measuring device calibration or offset detection. This may allow avoiding calibration errors that could result from a deviation from the equilibrium $CO_2$ concentration in the bioreactor gas phase caused by the additional headspace aeration.

In case during the initialization phase of the second bioreactor not only fresh medium but also additional liquids such as feeding solutions and/or acidic or basic liquids are added to the second bioreactor, the same amount and composition of said additional liquids is added to the first bioreactor during initialization to ensure that at the second and first time, the medium (including all the additional liquids and substances) in the second and first bioreactors is identical.

Figure 4:
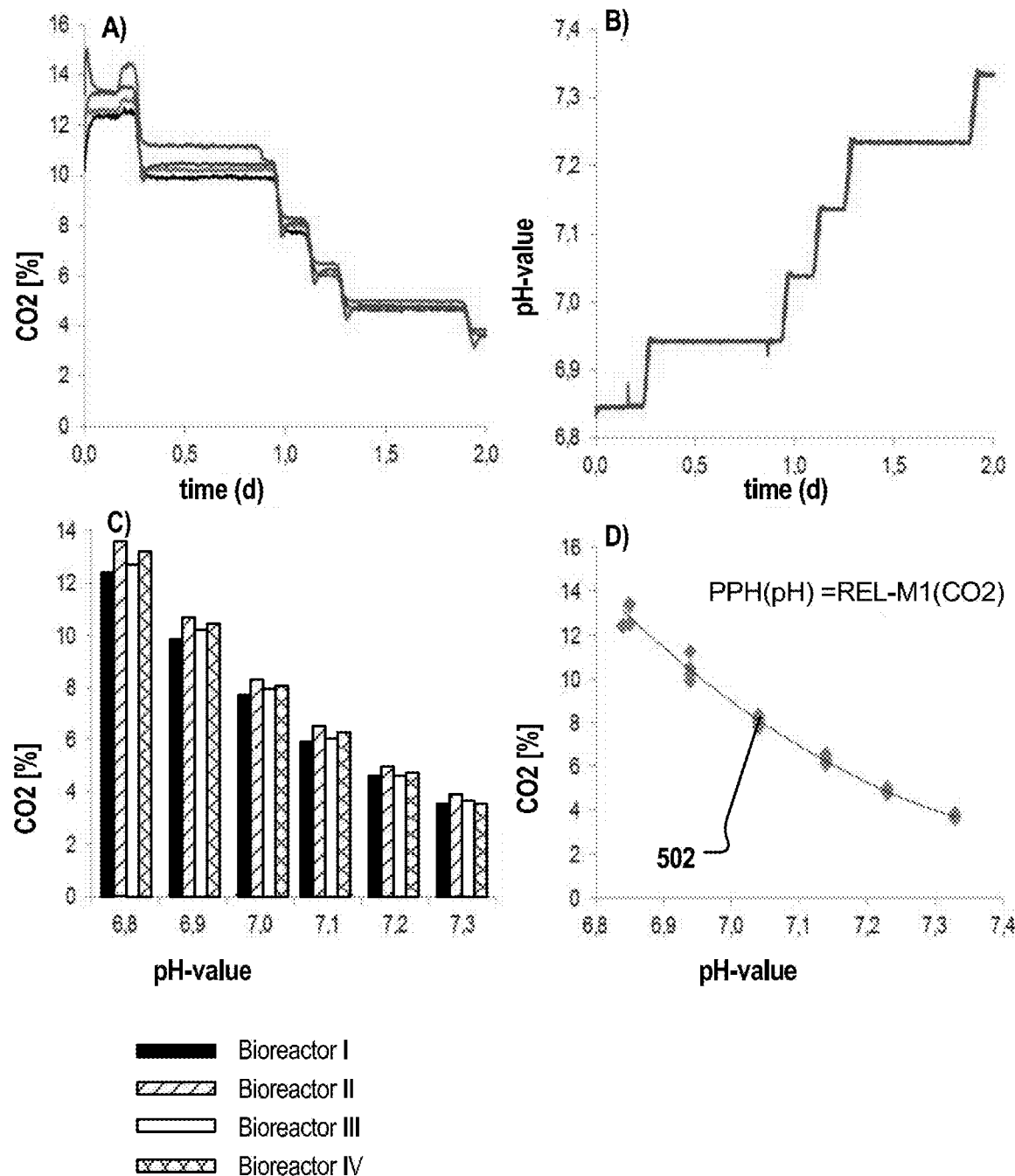
FIG. 4 shows diagrams illustrating the dependence of the CO2 concentration in the off gas of a bioreactor from the pH value.

FIG. 4 shows diagrams A, B, C and D illustrating the dependence of the $CO_2$ concentration in the off gas of four different bioreactors I-IV from the pH value and the independence of said $CO_2$ concentration of engineering—and size parameters of the respective bioreactors.

The four different bioreactors have the following engineering properties:

|  | Bioreactor I | Bioreactor II | Bioreactor III | Bioreactor IV |
| --- | --- | --- | --- | --- |
| Total volume (volume of medium + gasphase) | 0.94 L | 1.2 L | 1.5 L | 1.8 L |
| Aeration rate | 26.3 mL/L/min | 20.8 mL/L/min | 16.6 mL/L/min | 13.8 mL/L/min |
| Number of stirrers | 1 | 1 | 2 | 2 |

Each of said bioreactors I-IV was filled with a particular cell culture medium M1 which did not comprise any cells. The original pH value of said medium was 6.85 (see diagram B). Then, the pH value was increased in each of the bioreactors by decreasing the $CO_2$ concentration in the gas volume above said medium in the respective bioreactor. At the beginning of the test and for each of a set of predefined pH values, the medium in each bioreactor was allowed to reach pH-$CO_2$ equilibrium with the gas volume above the medium at a predefined temperature and pressure, e.g. 20° C. and normal atmospheric pressure. After said equilibrium was reached, the $CO_2$ concentration in Vol. % of the total off gas (also referred to as "fraction $CO_2$ gas", "$CO_2$[%]" or "$FCO_2$") was determined for each of said four bioreactors (see diagram A showing, in combination with diagram B, the impact of the pH-value on the measured $CO_2$ concentration in the off gas). Diagram 4 C) shows the impact of the pH-value on the measured $CO_2$ concentration of each of the four bioreactors in the form of a bar chart. The maximum deviation of the $CO_2$ [%] obtained for each of the four bioreactors was less than 0.4% of the total off gas of the bioreactor.

The diagram 4 D) is a plot comprising the $CO_2$ [%] values measured at each of the four bioreactors I-IV at each of a set of pH values (6.85, 6.95, 7.05, 7.15, 7.25, 7.35) at a time when the medium M1 of said bioreactor reached pH-$CO_2$ equilibrium state.

It should be noted that the pH-$CO_2$ equilibrium in a bioreactor may be challenged by the rate of $CO_2$ gas entering and/or leaving the bioreactor, so the pH-$CO_2$ equilibrium may in fact be a dynamic equilibrium. Nevertheless, it is possible to control a bioreactor in a manner that the dynamic pH-$CO_2$ equilibrium is established at a particular pH value, e.g. by decreasing or increasing the $CO_2$ concentration in the gas volume above the medium in the bioreactor by modifying the total $CO_2$ influx rate in the bioreactor. Alternatively, the pH value may be modified by adding acidic or basic substances or liquids.

Preferentially, the dynamic pH-$CO_2$ equilibrium state is established in a bioreactor at a particular pH value solely by controlling the $CO_2$ influx rate and total gas outflux rate in a manner that a desired pH value is reached. Using the $CO_2$ concentration for establishing the pH-$CO_2$ equilibrium rather than adding a basic or an acidic substance has the advantage that the composition of the medium is not altered (except for the concentration of the solved $CO_2$ and its dissociation products) and thus the medium specific relation can be empirically derived from the same medium at different pH values.

Then, a curve 502 is fitted to the plot in order to empirically determine parameters for a relation 316 being specific for the medium M1 contained in the four bioreactors. This approach allows to empirically determine, for a particular cell culture medium, a medium-specific relation 136 used as input by the comparison unit for predicting the absolute pH value of a medium given a measured $CO_2$ off gas concentration when said medium has a particular pressure and temperature (e.g. 20° C. and normal atmospheric pressure), lacks any cells and is in pH-$CO_2$ equilibrium with the gas phase. The obtained relation is independent of bioreactor scale, aeration rate and other engineering parameters.

The medium-specific relation is determined only once for a particular medium M1. The determination may be performed in a single bioreactor, e.g. in the second bioreactor 102 before the second bioreactor is inoculated with the cell culture. In order to increase accuracy, it is also possible to perform the determination in multiple bioreactors or other containers allowing the measurement of a pH value and a $CO_2$ gas fraction ($CO_2$ concentration) and then use the information obtained in the multiple bioreactors or containers for obtaining a more accurate, fitted curve 502. In the example depicted in FIGS. 4D and 5, four different bioreactors were used for empirically determining a fitted curve 502 and a corresponding, medium-specific relation between equilibrium pH value and equilibrium $CO_2$ concentration.

A further, similar test (not shown) was performed with four bioreactors having a volume of 400 L, 100 L, 2 L and 2 L and comprising the same type of medium. The bioreactors comprised pH measuring devices of different types (e.g. Knick and Mettler probes), comprised different controller setup configurations (Siemens S7 vs. Sartorius DCU) and different off gas analyzers of the same type (Dasgip/Eppendorf GA4). The pH measuring devices were calibrated respectively using conventional calibration buffers at two known pH points (4 and 7) before they were submerged in the medium of their respective bioreactor. In a next step, each of the four pH measuring devices was recalibrated by the use of a fifth, pre-calibrated pH measuring device that was sequentially inserted into the media of the four compared bioreactors. All four pH measuring devices were recalibrated onto the value of the fifth pH measuring device. After that recalibration, the $CO_2$ concentration in the off gas ("$FCO_2$" value) of all four bioreactors was measured. The four obtained $FCO_2$ measurement values showed a difference ("delta") of the maximal value of all four values to the minimal value of all four values of about 0.75%.

Then, the controller deviation of the four bioreactors was minimized to establish comparable actual pH values in all four bioreactors. After that minimization, the $CO_2$ concentration in the off gas ("$FCO_2$" or "$CO_2$ [%]") of all four bioreactors was measured. The four obtained $FCO_2$ measurement values showed a difference ("delta") of the maximal value of all four values to the minimal value of all four values of about 0.27%. The results confirmed that bioreactors, whose media are in pH-CO2 equilibrium state have the same $CO_2$ concentration at the same pH values independent of media volume, overall volume, aeration rate and parameters that depend on aeration rate, stirrer speed and parameters that depend on stirrer speed and further parameters that depend on scale, bioreactor dimension and the like.

Therefore in said equilibrium state, with a variability of 0.27%, pH offsets of less than 0.02 pH scale units were detectable in this test scenario. Thus, a highly accurate method for calibrating pH measuring devices is provided.

Figure 5:
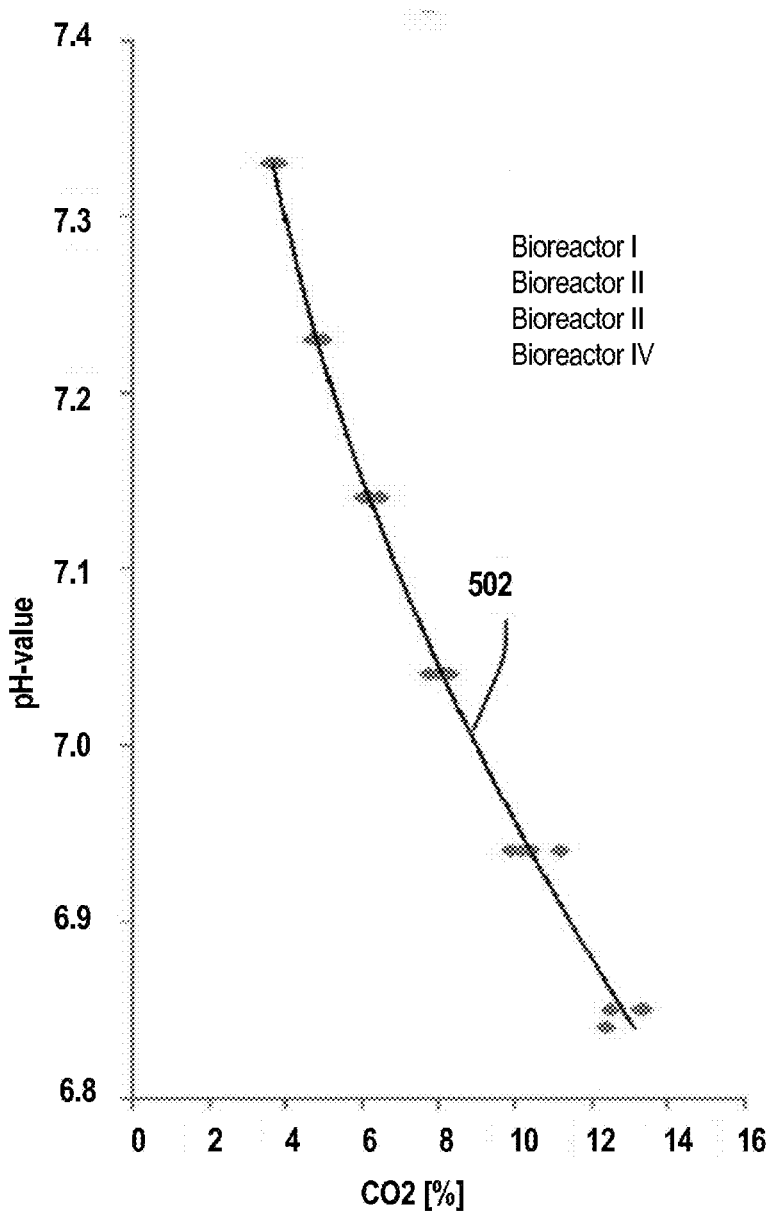
FIG. 5 shows a plot used for obtaining a medium-specific pH-CO2 concentration relation.

FIG. 5 is a transformed version of the diagram in FIG. 4 D). The medium-specific relation 136 of medium M1 is an equation PPH(pH)=REL-M1(CO2) obtained by mathematically fitting multiple empirically determined pairs of a pH-value and a respective CO2 concentration [%] in the gas phase above said medium, the CO2 concentration in the gas phase being in pH-CO2 equilibrium with said medium according to the Henderson-Hasselbalch equation.

The equation derived empirically by fitting a linear or polynomial curve to the plot of FIG. 5 allows predicting a pH value of a medium at the predefined temperature and the predefined pressure in case the gas volume above said medium is in pH-CO2 equilibrium state with said medium and has a particular CO2 concentration. The prediction is specific for the medium M1 for which the relation was empirically obtained.

The "CO2" parameter is an input parameter of said equation for inputting a CO2 concentration measured in a gas phase being in pH-CO2 equilibrium state with the medium of a bioreactor.

"REL-M1" is a set of one or more parameters a1, a2, b1, b2, b3 connected by operators. The parameters have been obtained by adjusting samples of the medium M1 lacking the cell culture to multiple different pH values as described above, thereby letting the samples reach pH-CO2 equilibrium at the predefined pressure and temperature, by determining the equilibrium CO2 concentrations in respective gas volumes being in contact with the medium in the samples, by plotting the measured equilibrium CO2 concentrations against the respective equilibrium pH values of the samples for generating the plot depicted in FIG. 5, fitting a curve 502 in the plotted values and deriving the parameters a1, a2 or b1, b2, b3 from the fitted curve.

According to some embodiments, the equation $PPH_{M1}(CO2)$=REL-M1(CO2) is a linear equation according to $PPH_{M1}(CO2)[\%]=a1 \times CO2 [\%]+a2$. In this case, the parameters a1 and a2 are the parameters derived from the fitted curve. In the depicted example, a linear fit would yield the following equation: $PPH_{M1}(CO2)=-0.046 \times CO2[\%]+7.45$. In this example, a1=−0.046 and a2=7.45.

According to other embodiments, the equation $PPH_{M1}(CO2)$=REL-M1(CO2) is a polynomial equation according to $PPH_{M1}(CO2)=b1 \times CO2[\%]^2 b2 \times CO2[\%]+b3$.

Using a polynomial fit has the advantage that it is more accurate than a linear fit, although a linear fit is already sufficiently accurate for calculating an absolute pH value by using solely the medium-specific relation 136 and a CO2 concentration $CO2_{R-M-ti}$ measured e.g. in the off gas of a bioreactor as input.

Figure 6:
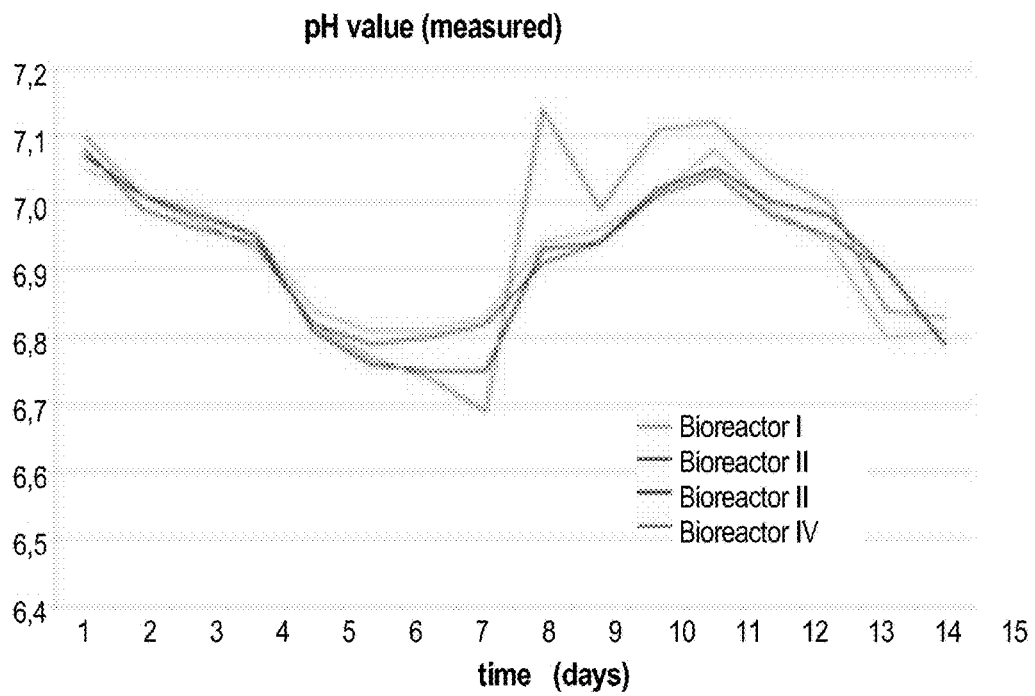
FIG. 6 shows pH values of four different bioreactors measured by respective pH meters while growing a cell culture in the respective bioreactors.

FIG. 6 shows the variation of a pH value measured in four different bioreactors I-IV while growing a cell culture in a particular medium M1 over multiple days for a particular cell culture project. Preferentially, each pH value is measured using a pH-measuring device, e.g. a potentiometric pH-meter, immersed in the medium M1 of the bioreactor at pH-CO2 equilibrium of said medium. In each bioreactor, at least a current pH value and a current CO2 concentration in the off gas are measured repeatedly before and after inoculation and during the whole project.

For example, the project could be to grow CHO cells (Chinese hamster ovary cells) over 14 days in the cell culture medium M1 under optimal or nearly optimal cell growth conditions until a cell density of about $100 \times 10^5$ cells/milliliter is reached.

Figure 7:
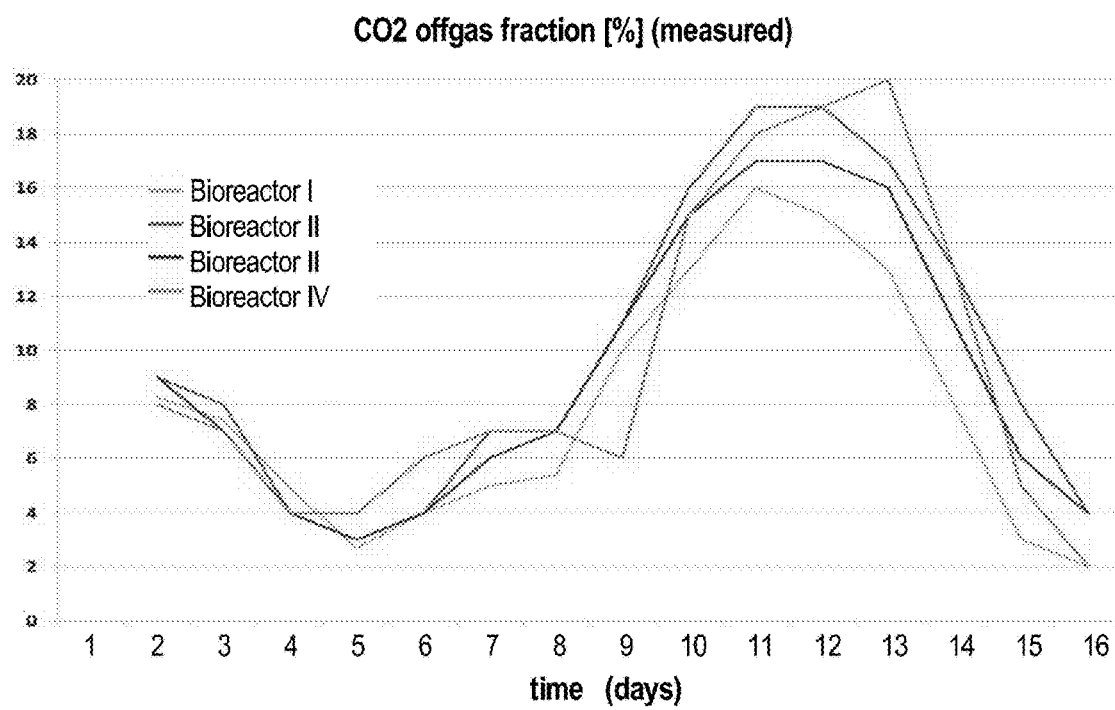
FIG. 7 shows the CO2 fraction measured in the off gas of each of the four bioreactors.

FIG. 7 shows the CO2 fraction ("CO2 concentration") measured in the off gas of each of the four bioreactors whose pH value profiles are shown in FIG. 6. The pH values and CO2 off gas concentrations measured for a particular bioreactor at a particular moment in time depend on each other as the CO2 concentration in the gas volume above the medium influences the pH value in accordance with the Henderson-Hasselbalch equation. Moreover, the cell metabolism may have an impact both on the pH value (via excreted metabolites such as lactate) and on the CO2 concentration in the gas phase (via aerobic degradation of substrates).

While growing the cells in one of the bioreactors, e.g. in a reference bioreactor 102, the current pH value and the current CO2 off gas concentrations in the reference bioreactor 102 may be determined repeatedly and a derivative parameter value is calculated from at least said two input parameter values and used as a parameter being indicative of a current status of the cell culture in the reference bioreactor. A profile of said derivative parameter values is generated. A profile is a representation of the variation of said parameter values versus time.

Figure 8A:
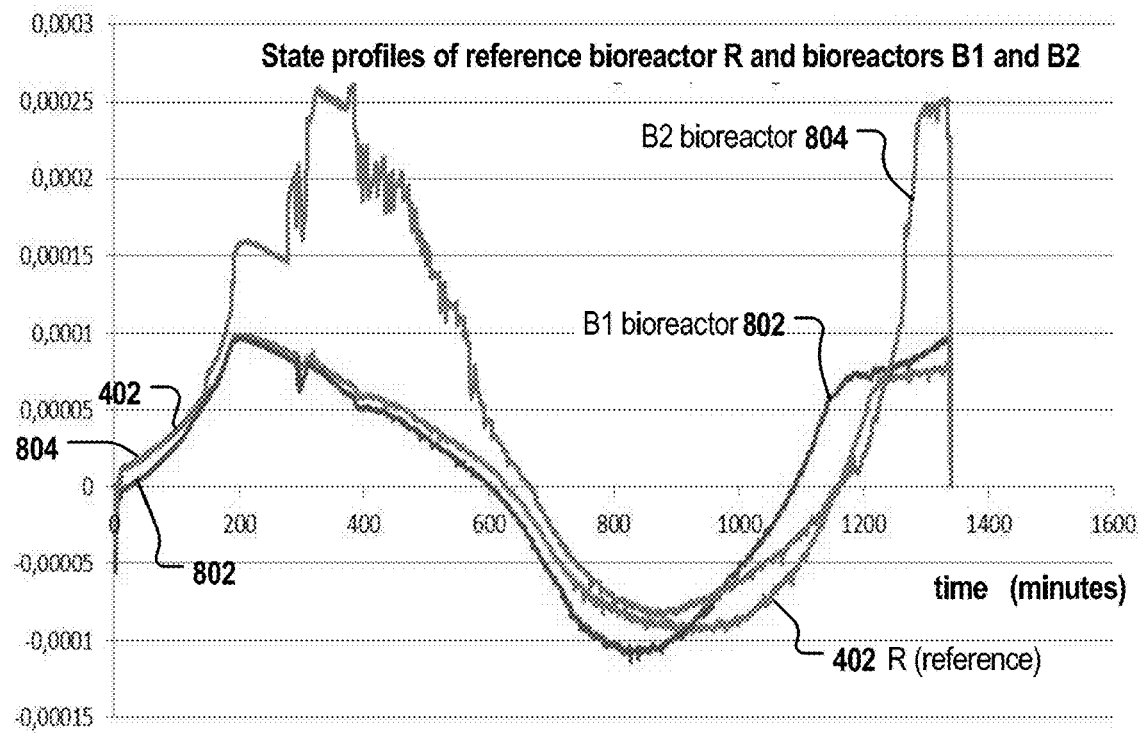
FIG. 8a is a diagram showing CO2-off gas-derived state profiles of two bioreactors and of a reference bioreactor.

FIG. 8a is a diagram showing a reference state profile 402 of a reference bioreactor 102, a state profile 802 of a first monitored and/or controlled bioreactor 104 and a further state profile 804 of a first monitored/and controlled bioreactor 106. Each state profile is indicative of the state of a bioreactor and its cell culture, whereby the state at a particular time ti is calculated as a derivative of at least a currently measured pH value and a currently measured CO2 concentration in the off gas of the bioreactor. All bioreactors R, B1 and B2 comprise the same medium M1, are operated at the same temperature and pressure and are in pH-equilibrium state with a respective gas volume at time t0. The time t0 represents a moment in time just before the respective bioreactor is inoculated with a cell culture.

At the moment t0, the reference bioreactor R, also referred to as "second bioreactor", the first bioreactor B1 and the third bioreactor B2 are configured and operated such that they have the same CO2 concentration in the off gas. The pH meters of the respective bioreactors R and B2 may measure an almost identical pH value at time t0. However, the pH measuring device of the bioreactor B1 may measure a different pH value at t0 than measured by the pH measuring device of the reference bioreactor (not shown). The pH measuring devices of the three bioreactors may be online pH meters immersed in the medium of the respective bioreactor. In this case, the comparison unit may determine that there is no calibration difference between the pH meters of the second/reference bioreactor R and the pH meter of the first bioreactor B2, but there exists a calibration deviation between the pH meters of the reference bioreactor R and the bioreactor B1.

In the depicted example, the profile value of state profile 804 of the monitored bioreactor 106 ("B2") at time t0 is identical to the reference value of the reference profile 402 at time t0. The value of profile 802 of the monitored bioreactor 104 ("B4") at time to significantly differs the reference value of the reference profile 402 at time t0.

Alternatively, instead of the profile values, the CO2 concentration of the off gas of the two bioreactors as depicted in FIG. 7 can be compared to determine if the pH measuring devices of the two compared bioreactors were calibrated identically. The two bioreactors are initiated and filled with the same cell-free medium at the same pressure and temperature and a current pH value and a current CO2 concentration of the medium in the two bioreactors are measured and compared when the two bioreactors have reached pH-CO2 equilibrium. If the CO2 concentration in the off gas of the two bioreactors are identical while the pH value are not, or if the pH values of the two bioreactors are identical and the CO2 concentration in the off gas are not, the comparison unit determines that the two bioreactors were calibrated differently.

Wrongly calibrated pH measuring devices may result in inaccurate results when comparing the cell culture states of two cell cultures based on cell culture profiles having been derived—solely or in addition to other parameters—from the pH values. As a consequence, also any action taken by the controller to minimize the state difference may fail to minimize the state differences (this effect is not shown in FIGS. 8a and 8b, because during the growing of the cell culture in bioreactor B2, the pH-CO2 equilibrium was modified by adding a base and increasing the total gas influx rate; thus, the profile of B2 significantly differs from the reference profile although the pH meters of the reference bioreactor and of bioreactor B2 were calibrated in the same way.

Wrongly calibrated pH meters may result in inaccurate results when comparing the cell culture states of two cell cultures based on the pH values of the respective bioreactors or any other monitoring or control parameter being a derivative of said pH values. As a consequence, also any action taken by the controller to minimize the pH difference may fail or may result in an even larger state deviation of the two compared bioreactors (this effect is not shown in FIGS. 8a and 8b, because during the growing of the cell culture in bioreactor B2, the pH-CO2 equilibrium was modified by adding a base and increasing the total gas influx rate; thus, the cell culture state profile of B2 significantly differs from the reference state profile although the pH meters of the reference bioreactor and of bioreactor B2 were calibrated in the same way).

For example, the state profile of a bioreactor before and after inoculation with a cell culture may be calculated as a PACO profile. A PACO value $PACO_{B1-ti}$, $PACO_{B2-ti}$ is indicative of a deviation of a CO2 off gas rate $ACO_{B1-M-ti}$, $ACO_{B2-M-ti}$ measured in the bioreactor from a predicted CO2 off gas rate $ACO_{B1-EXP-ti}$, $ACO_{B2-EXP-ti}$. The predicted CO2 off gas rate is the off gas rate of said medium in the bioreactor in pH-CO2 equilibrium state under absence of the cell culture and under the condition that the pH value of the medium in equilibrium state is identical to the pH value of the bioreactor 104, 106 when measuring the CO2 off gas rate in the bioreactor. The PACO value depends on the amount of CO2 off gas produced by the cells of the cell culture in the bioreactor while cultivating the cell culture. The computation of the PACO value $PACO_{B1-ti}$, $PACO_{B2-ti}$ uses as input:
the received current CO2 off gas rate $ACO_{B1-M-ti}$, $ACO_{B2-M-ti}$;
the received current pH value $pH_{B1-ti}$, $pH_{B2-ti}$;
the total gas inflow rate $TGI_{B1}$, $TGI_{B2}$ of the bioreactor at the time ti of receiving the current CO2-off gas rate; and
the medium-specific relation 136.

The computation of the PACO value of the monitored and/or controlled bioreactor at a current time comprises computing, for each of the received current CO2 off gas rates and pH values of the monitored and/or controlled bioreactor:
the expected CO2 off gas fraction $FCO2_{B1-EXP-ti}$ of a current outgas volume of the bioreactor 104 according to: $FCO2_{B1-EXP-ti} = REL\text{-}M1(pH_{B1-ti})$, wherein $FCO2_{B1-EXP-ti}$ is a predicted CO2 off gas fraction of the total off gas volume ($TGO_{B1}$) of the bioreactor 104 in % at the current time ti, the prediction being calculated by using the received current pH value $pH_{B1-ti}$ as input for REL-M1($pH_{B1-ti}$), wherein REL-M1 is a medium-specific relation of the medium M1 derived empirically by fitting a plot such as depicted, for example, in FIG. 4 D. The parameter $pH_{B1-ti}$ is the received current pH value in the medium of the bioreactor 104, 106 at a time ti; thus, the expected CO2 off gas fraction in the bioreactor is computed under the assumption that the medium of the bioreactor lacks the cell culture, has the pH value used as input of the medium-specific relation and is in pH-CO2 equilibrium state with the gas phase in the bioreactor above said medium and thus is also in equilibrium with the total off gas volume of said bioreactor.
an expected CO2 off gas rate $ACO_{B1-EXP-ti}$ [mol/min] value according to:

$$ACO_{B1-EXP-ti}[\text{mol/min}] = \left(\frac{FCO2_{B1-EXP-ti[\%]}}{100}\right) \times TGI_{B1},$$

wherein the $ACO_{B1-EXP-ti}$ value is the expected CO2 off gas rate of the bioreactor (104) when the medium of the bioreactor has the currently measured pH value and is in pH-CO2 equilibrium with the gas phase above said medium, wherein the $TGI_{B1}$ is the total amount of gas influx of the bioreactor 104 at the current time (ti); the total amount of gas influx of the bioreactor is approximately identical to the total amount of gas outflow;
the $PACO_{B1-ti}$ value according to: $PACO_{B1-ti} = ACO_{B1-EXP-ti} - ACO_{B1-M-ti}$, wherein $ACO_{B1-M-ti}$ is the CO2 off gas rate measured at time ti in the bioreactor 104.

A reference $PACO_{B1-ti}$ value of the reference bioreactor 102 can be computed accordingly: $PACO_{R-ti} = ACO_{R-EXP-ti} - ACO_{R-M-ti}$, wherein $ACO_{R-M-ti}$ is the CO2 off gas rate measured at time ti in the bioreactor 102.

According to some embodiments, the above mentioned comparison of PACO values is performed repeatedly after inoculation of the cell culture for identifying state deviations of the cell culture in bioreactor 104 compared to the corresponding cell culture state in the reference bioreactor 102.

A "PACO value" value is a data value. A "FCO2 value" is a data value. An "ACO vale" is a data value. "FCO2" or "CO2 [%]", also referred to as "CO2 concentration" is the "fraction CO2 gas" in a gas volume, e.g. in the off gas of a bioreactor.

A "profile" is a set of data values or a mathematical relation that indicates the variation of a parameter value over time. The parameter value can be, for example, a PACO value, a CO2 concentration in the off gas ("FCO2"), a CO2 off gas rate ("ACO value") or the pH value obtained from a bioreactor.

Figure 8B:
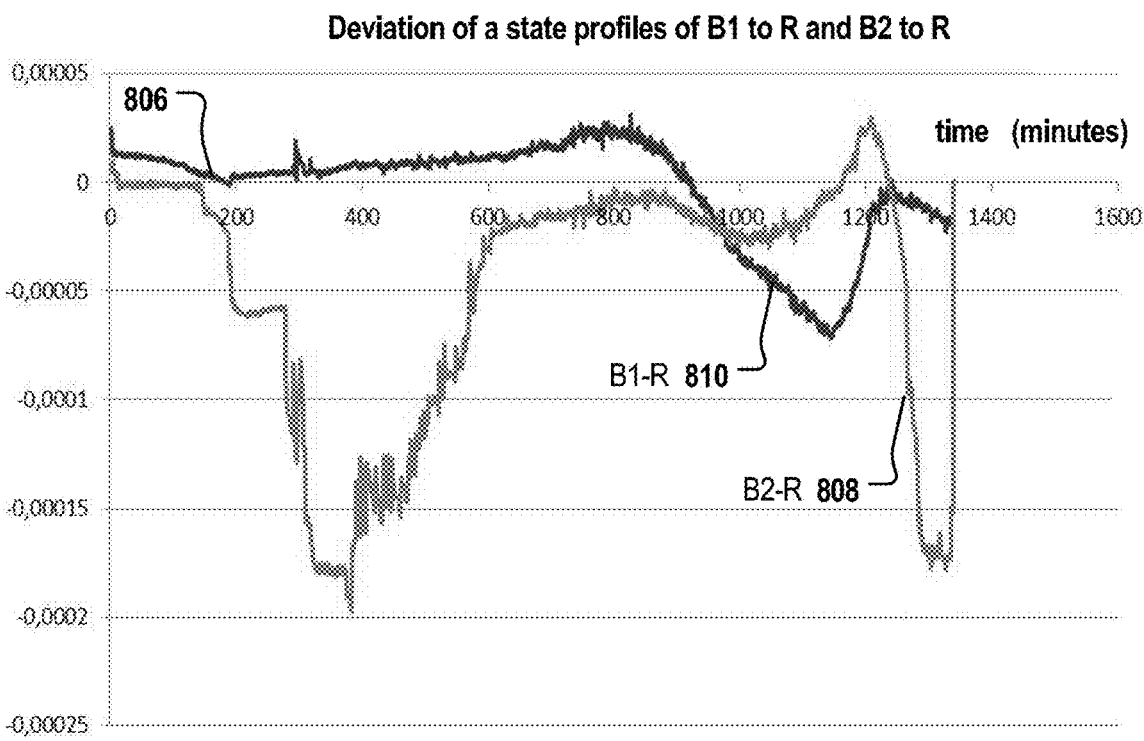
FIG. 8b is a diagram showing the state profile differences of the two bioreactors of FIG. 8a to said reference bioreactor.

FIG. 8b is a diagram showing the profile differences of the cell culture state profiles 802, 804 of two bioreactors 104, 106 to the reference profile 402 of the reference bioreactor 102. Curve 810 represents profile differences of the bioreactor 104 and the reference bioreactor and curve 808 represents profile differences of the bioreactor 106 and the reference bioreactor. The profile differences of the bioreactor 106 to the reference profile 402 are significantly larger than the differences of the bioreactor 104, because while growing the cell culture in B2, the pH-CO2 equilibrium was modified. Comparing a PACO profile with a reference PACO profile allows identifying cell culture state deviations in two compared bioreactors and to automatically, semi-automatically or manually take the appropriate actions to minimize profile differences. It has been observed that calibration differences between the pH measuring devices may result in significant differences in control parameter profiles, e.g. PACO profiles. Thus, using a calibration method according to embodiments of the invention in the bioreactor initialization phase may significantly increase the accuracy of comparing and synchronizing bioreactor and cell culture states at a later moment in time.

Figure 9:
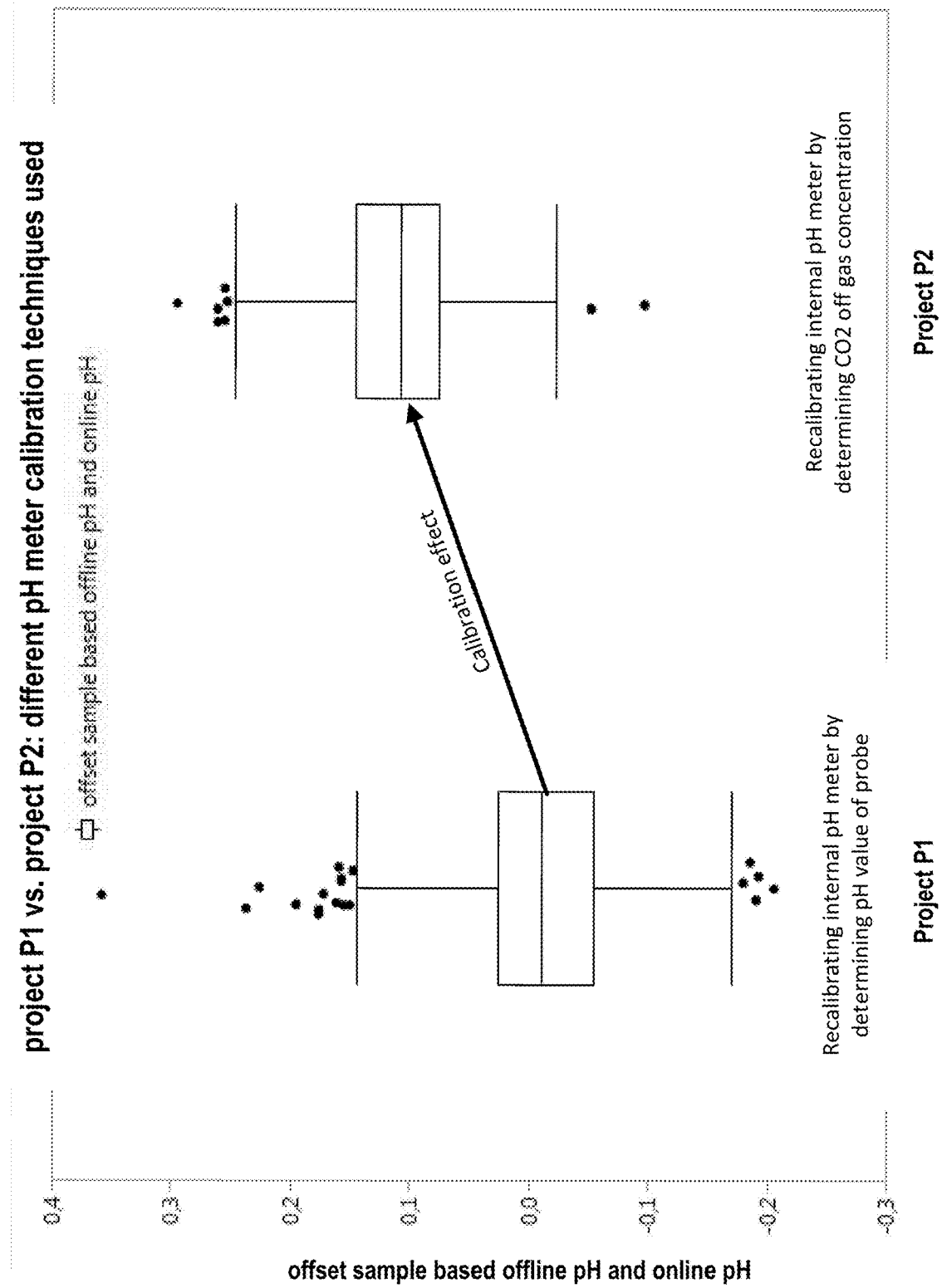
FIG. 9 is a plot that illustrates that the sampling process results in a deviation of the pH value measured in the sample from the pH value in the tank and that the way the pH measuring devices are calibrated also has an impact on the measured pH value.

FIG. 9 depicts two box and whisker plots that illustrate that the sampling process has an effect on the measured pH value.

While performing a first cell culture project P1, the pH value of the medium of a bioreactor comprising the cell culture was repeatedly measured with a bioreactor-internal pH meter. The pH values measured by the bioreactor-internal pH meter at multiple time points t1, t2, to were compared with pH values measured by a second, bioreactor-external pH meter in medium samples drawn at said respective time points t1, . . . , tn. Thus, the data values represented by the box and whisker plot of project P1 respectively represent the difference between the pH value measured by the bioreactor-internal and the bioreactor-external pH meter at a respective time t1, . . . , tn. Thus, the box and whisker plot for project P1 depicts the variability and distribution of pH differences ("pH offset effects") generated by the sampling process. The samples were tempered at 32° C. to ensure a constant pH measurement temperature for all measurements.

The bioreactor-internal pH meter of project P1 was calibrated according to a state of the art method, i.e., by removing the bioreactor-internal pH meter from the bioreactor, calibrating the pH meter outside of the bioreactor with a reference solution of known pH, re-introducing the calibrated pH meter into the bioreactor and autoclaving the bioreactor.

Moreover, in project P1, the pH values measured by the bioreactor-internal pH meter were repeatedly compared with pH values measured by the bioreactor-external pH meter in samples of the medium of the bioreactor. In case the comparison revealed that a difference (i.e., "offset") between the two compared pH values is higher than a given threshold, the bioreactor-internal pH meter was recalibrated. Before inoculation, recalibration of the bioreactor-internal pH meter took place no matter the offset ("focus calibration"). The pH offset of project P1 averages around "−0.01" and thus is very close to zero. This is not surprising as the pH measurement values obtained by the bioreactor-external pH meter was used as a reference for calibrating the bioreactor-internal pH meter, thereby largely leveling out the offset effects. A disadvantage of this calibration approach is, however, that the absolute, "real" pH value of the medium in the bioreactor and the strength of the offset effect remains unknown. The variability is very high with only 50% of all data points within +/−0.05 pH, whereas more than 25% of all offsets are greater than 0.07 pH scale units.

A disparity between on-line and off-line pH measurements (performed by bioreactor-internal and bioreactor-external pH meters) was also observed and confirmed e.g. by Heather Evans et al.: "Dealing with Disparity in On-line and Off-line pH Measurements Genentech found pH drift in its on-line measurements for a cell culture process, and continues to investigate its cause" when performing similar pH measuring and pH meter calibration tests like described for project P1. Heather Evans et al. considered the ability to control the pH within a range of +/−0.10 pH units as critical for ensuring a consistent and robust process performance in terms of both productivity and product quality.

The box and whisker plot of the second project P2 was obtained as described for project P1. However, instead of calibrating the bioreactor-internal pH meter according to the state of the art approach, the bioreactor-internal pH meter is calibrated according to an embodiment of the invention using a computed, expected CO2 offgas rate that was computed for the medium used and for the current temperature and pressure by taking as input a measured CO2 concentration in the off gas of the bioreactor. Thus, the calibration of the bioreactor-internal pH meter was repeatedly performed (after media fill and the establishment of a pH-CO2 equilibrium and before inoculation with a cell culture as cell metabolites would shift the equilibrium) using a medium specific relation between the pH value and the CO2 off gas rate as described for embodiments of the invention.

The observed pH offset between the extra- and intra-bioreactor pH meter averages around +0.11, thereby revealing that the strength of the offset effect is more than 0.1 pH units high. As for P1, the samples were taken at 32° C. and the pH meters used were glass electrodes. The variability of offline pH measurement stays comparable, as the sampling procedure and offline pH measurement method in P1 and P2 are the same.

Altogether, 1070 data values were obtained for generating the two box and whisker plots for projects P1, P2 in FIG. 9 (P1: N=607 and P2: N=463). In both projects, glass electrodes were used at defined temperature as the intra and extra-bioreactor pH meters.

As can be inferred from the two plots, the variability of the pH offsets determined in both projects P1, P2 is similar. The pH value offsets are caused by the sampling process in both cases.

However, as can also be inferred from FIG. 9, the mean of the pH offsets of project P1 differs from the mean of the offsets obtained for project P2 by almost 0.1 scale units. This "difference of pH offset means" is caused by different methods used for calibrating the bioreactor-internal pH meters in projects P1 and P2. Differences of the mean pH values would also be caused by changing the sampling method, e.g. by increasing the time between taking a sample and actually performing the pH measurement in the sample.

As can be inferred from FIG. 9, offline pH measurements can be assumed to be the root cause for pH variability. The shift in average offset is due to general offsets that are added by sampling, sample hold times, temperature drops, carbon dioxide degassing during sampling and offline measurement, as well as specific offsets of the used offline measurement method. Blood gas analyzer data (not shown) deliver different offsets. Other offline pH measurement methods (not shown) deliver again different offsets.

LIST OF REFERENCE NUMERALS 100 system for monitoring and/or controlling cell culture states in a bioreactor
102 first ("reference") bioreactor
104 second bioreactor B1
106 further bioreactor B2
108 pH-measuring device
110 processor
112 memory
114 storage medium
120 interface for receiving one or more medium-specific relations
122 CO2 off gas analyzer
124 CO2 off gas analyzer
126 CO2 off gas analyzer
128 interface for receiving measurement parameters from two or more bioreactors
130 comparison unit
132 control unit
134 display
136 medium-specific relation for medium M1
138 medium-specific relation for medium M2
140 sensor for total gas influx
142 pH-measuring device
144 sensor for total gas influx
146 pH-measuring device
202-206 steps
402 state profile of reference bioreactor 102
502 medium-specific relation plotted for four bioreactors
802 state profile of a bioreactor
804 state profile of a bioreactor
808 state profile difference to reference profile
810 state profile difference to reference profile
M1 cell culture medium
$TGI_{B1}$ total gas influx into bioreactor B1
$TGI_{B2}$ total gas influx into bioreactor B2
$TGI_R$ total gas influx into the reference bioreactor
$TGO_{B1}$ total off gas of bioreactor B1
$TGO_{B2}$ total off gas of bioreactor B2
$TGO_R$ total off gas of reference bioreactor
$TLI_{B1}$ total liquid influx into bioreactor B1
$TLI_{B2}$ total liquid influx into bioreactor B2
$TLI_R$ total liquid influx into the reference bioreactor
$TLO_{B1}$ total (liquid) outflow of bioreactor B1
$TLO_{B2}$ total (liquid) outflow of bioreactor B2
$TLO_R$ total (liquid) outflow of reference bioreactor

The invention claimed is:

1. A method for determining if a first pH measuring device operatively coupled to a first tank is affected by a pH measuring problem, the problem being that the first pH measuring device is calibrated differently than a second pH measuring device operatively coupled to a second tank, the method comprising:
receiving, by a comparison unit, a first CO2 concentration and a first pH value, the first CO2 concentration being a CO2 concentration of a first gas volume above a medium in the first tank, the first CO2 concentration and the first pH value being measured at a first time, the first time being a time when the medium in the first tank is in pH-CO2 equilibrium state with the first gas volume at a predefined temperature and pressure, said equilibrium state being unaffected by the metabolism of any cell culture, the first pH value being a measured value provided by the first pH measuring device;
receiving, by the comparison unit, a second CO2 concentration and a second pH value, the second CO2 concentration being a CO2 concentration of a second gas volume above the same type of medium contained in the second tank, the second CO2 concentration and the second pH value being measured at a second time, the second time being a time when the medium in the second tank is in pH-CO2 equilibrium state with the second gas volume at the predefined temperature and pressure, said equilibrium state being unaffected by the metabolism of any cell culture, the second pH value being a measured value provided by the second pH measuring device;
comparing, by the comparison unit, the first and second pH values and comparing the first and second CO2 concentrations for determining that the first pH measuring device is affected by the pH measuring problem;
calibrating the first pH measuring device based on determining that the first pH measuring device is affected by the pH measuring problem; and
measuring a calibrated first pH value using the calibrated first pH measuring device.

2. The method of claim 1, the determination that the first pH measuring device has the pH measuring problem being made in case:
the first and second CO2 concentrations are identical and the first and second pH values differ from each other by more than a threshold value; or
the first and second pH values are identical and the first and second CO2 concentrations differ from each other by more than a further threshold value; or
a first data value differs from a second data value by more than a further threshold, the first data value being derived from the first pH value and the first CO2 concentration, the second data value being derived from the second pH value and the second CO2 concentration.

3. The method of claim 1,
the first tank being a bioreactor or a harvest tank and/or the second tank being a reference bioreactor or a reference harvest tank.

4. The method of claim 1, further comprising:
receiving a third CO2 concentration and a third pH value, the third CO2 concentration being a CO2 concentration of a third gas volume above the medium in the first tank, the third CO2 concentration and the third pH value being measured at a third time, the third time being a time when the medium in the first tank is in pH-CO2 equilibrium state at the predefined temperature and pressure with the third gas volume and after said equilibrium state is modified by the metabolism of a cell culture in the first tank, the third pH value being a measured value provided by the first pH measuring device;
receiving a fourth CO2 concentration and a fourth pH value, the fourth CO2 concentration being a CO2 concentration of a fourth gas volume above the medium in the second tank, the fourth CO2 concentration and the fourth pH value being measured at a fourth time, the fourth time being a time when the medium in the second tank is in pH-CO2 equilibrium state at the predefined temperature and pressure with the second gas volume and after said equilibrium state is modified by the metabolism of the cell culture in the second tank, the fourth pH value being a measured value provided by the second pH measuring device, a lapsed time between the third time and inoculation of the first tank being identical to a lapsed time between the fourth time and inoculation of the second tank;

receiving a measured first oxygen uptake rate of the cell culture in the first tank at the third time;
receiving a measured second oxygen uptake rate of the cell culture in the second tank at the fourth time;
in case the first and second oxygen uptake rates are identical, comparing the third and fourth pH values and CO2 concentrations for determining if the first and second pH measuring devices are calibrated differently.

5. The method of claim 1, the first pH measuring device being at least partially surrounded by the medium within the first tank, wherein:
the first tank lacks means for manually or automatically taking a sample of the medium in the second tank; or
the first tank comprises means for manually or automatically taking a sample of the medium in the first tank, the method further comprising: during a time interval after filling the medium in the first tank and before adding a cell culture to the medium in the first tank, keeping all openings of the means for manually or automatically taking a sample of the medium in the second tank closed.

6. The method of claim 1, the second pH measuring device being at least partially surrounded by the medium within the second tank wherein:
the second tank lacks means for manually or automatically taking a sample of the medium in the second tank; or
the second tank comprises means for manually or automatically taking a sample of the medium in the second tank, the method further comprising: during a time interval after filling the medium in the second tank and before adding a cell culture to the medium in the second tank, keeping all openings of the means for manually or automatically taking a sample of the medium in the second tank closed.

7. The method of claim 1, the method being used for determining if the second pH measuring device is calibrated differently than the first pH measuring device, the determination if the first and second pH measuring device are calibrated differently being performed while the second pH measuring device is at least partially surrounded by the medium in the second tank and without taking a sample of the medium of the second tank for performing said determination.

8. The method of claim 1, the determination if the first pH measuring device is affected by the pH measuring problem being performed by using the first and second CO2 concentrations and the first and second pH values as the only data input for said determination.

9. The method of claim 1, the method further comprising:
performing an online-measurement with the first pH measuring device for measuring the first pH value, the first pH measuring device being at least partially surrounded with the medium in the first tank; and/or
performing an online-measurement by a first CO2 sensor in the off gas of the first tank for providing the first CO2 concentration.

10. The method of claim 1, further comprising: performing an online-measurement with the second pH measuring device for measuring the second pH value, the second pH measuring device being at least partially surrounded with the medium in the second tank; and/or
performing an online-measurement by a second CO2 sensor in the off gas of the second tank for providing the second CO2 concentration.

11. The method of claim 1, the method comprising, in case of determining that the first pH measuring device is affected by the pH measuring problem, performing one or more of the following steps by the comparison unit:
outputting a warning message;
automatically performing or triggering the performing of the calibrating of the first pH measuring device;
automatically performing or triggering the performing of a replacement of the first pH measuring device by a new first pH measuring device.

12. The method of claim 1, the first tank differing from the second tank in respect to one or more of the following features:
a) the gas volume in the tank,
b) the medium volume in the tank,
c) the Reynolds number of the tank,
d) the Newton number of the tank,
e) the dimensions of the tank,
f) geometrical features of the tank and/or tank baffles,
g) the stirrer configuration,
h) the stirring rate,
i) the volumetric mass transfer coefficient for oxygen (kLa) of the tank,
j) total gas influx rate and/or O2 influx rate and/or N2 influx rate and/or CO2 influx rate,
k) power input,
l) pressure in the tank,
m) gas bubble hold time in the medium,
n) gas bubble size and distribution in the medium,
o) surface speed,
p) a parameter calculated as a derivative from one or more of the parameters a)-o);
q) the geographic location of the two tanks.

13. A system comprising: a first tank, a first pH measuring device, a second tank, and a second pH measuring device, and a comparison unit, the system configured for:
receiving, by the comparison unit, a first CO2 concentration and a first pH value, the first CO2 concentration being a CO2 concentration of a first gas volume above a medium in the first tank, the first CO2 concentration and the first pH value being measured at a first time, the first time being a time when the medium in the first tank is in pH-CO2 equilibrium state with the first gas volume at a predefined temperature and pressure, said equilibrium state being unaffected by the metabolism of any cell culture, the first pH value being a measured value provided by the first pH measuring device;
receiving, by the comparison unit, a second CO2 concentration and a second pH value, the second CO2 concentration being a CO2 concentration of a second gas volume above the same type of medium contained in the second tank, the second CO2 concentration and the second pH value being measured at a second time, the second time being a time when the medium in the second tank is in pH-CO2 equilibrium state with the second gas volume at the predefined temperature and pressure, said equilibrium state being unaffected by the metabolism of any cell culture, the second pH value being a measured value provided by the second pH measuring device;
comparing the first and second pH values and comparing the first and second CO2 concentrations for determining that the first pH measuring device is affected by a pH measuring problem, the problem being that the first pH measuring device operatively coupled to the first tank is calibrated differently than the second pH measuring device operatively coupled to the second tank;

calibrating the first pH measuring device based on determining that the first pH measuring device is affected by the pH measuring problem; and measuring a calibrated first pH value using the calibrated first pH measuring device.

14. The system of claim 13, further comprising:
a control unit operatively coupled to the comparison unit;
the control unit being configured to monitor and/or control a state of a cell culture in the first tank, thereby using pH values repeatedly measured by the first pH measuring device as input.

15. The system of claim 13, wherein the determination that the first pH measuring device has a pH measuring problem is made in case:
the first and second $CO_2$ concentrations are identical and the first and second pH values differ from each other by more than a threshold value; or
the first and second pH values are identical and the first and second $CO_2$ concentrations differ from each other by more than a further threshold value; or
a first data value differs from a second data value by more than a further threshold, the first data value being derived from the first pH value and the first $CO_2$ concentration, the second data value being derived from the second pH value and the second $CO_2$ concentration.

16. The system of claim 13,
the first tank being a bioreactor or a harvest tank and/or the second tank being a reference bioreactor or a reference harvest tank.

17. The system of claim 13, further configured to:
receive a third $CO_2$ concentration and a third pH value, the third $CO_2$ concentration being a $CO_2$ concentration of a third gas volume above the medium in the first tank, the third $CO_2$ concentration and the third pH value being measured at a third time, the third time being a time when the medium in the first tank is in pH-$CO_2$ equilibrium state at the predefined temperature and pressure with the third gas volume and after said equilibrium state is modified by the metabolism of a cell culture in the first tank, the third pH value being a measured value provided by the first pH measuring device;
receive a fourth $CO_2$ concentration and a fourth pH value, the fourth $CO_2$ concentration being a $CO_2$ concentration of a fourth gas volume above the medium in the second tank, the fourth $CO_2$ concentration and the fourth pH value being measured at a fourth time, the fourth time being a time when the medium in the second tank is in pH-$CO_2$ equilibrium state at the predefined temperature and pressure with the second gas volume and after said equilibrium state is modified by the metabolism of the cell culture in the second tank, the fourth pH value being a measured value provided by the second pH measuring device, a lapsed time between the third time and inoculation of the first tank being identical to a lapsed time between the fourth time and inoculation of the second tank;
receive a measured first oxygen uptake rate of the cell culture in the first tank at the third time;
receive a measured second oxygen uptake rate of the cell culture in the second tank at the fourth time;
in case the first and second oxygen uptake rates are identical, compare the third and fourth pH values and $CO_2$ concentrations for determining if the first and second pH measuring devices are calibrated differently.

18. The system of claim 13, the first pH measuring device being at least partially surrounded by the medium within the first tank, wherein:
the first tank lacks means for manually or automatically taking a sample of the medium in the second tank; or
the first tank comprises means for manually or automatically taking a sample of the medium in the first tank, the method further comprising: during a time interval after filling the medium in the first tank and before adding a cell culture to the medium in the first tank, keeping all openings of the means for manually or automatically taking a sample of the medium in the second tank closed.

19. The system of claim 13, the second pH measuring device being at least partially surrounded by the medium within the second tank wherein:
the second tank lacks means for manually or automatically taking a sample of the medium in the second tank; or
the second tank comprises means for manually or automatically taking a sample of the medium in the second tank, the method further comprising: during a time interval after filling the medium in the second tank and before adding a cell culture to the medium in the second tank, keeping all openings of the means for manually or automatically taking a sample of the medium in the second tank closed.

20. At least one non-transitory computer-readable storage medium comprising computer readable instructions that, when executed by at least one processor, are configured to cause the at least one processor to:
receive a first $CO_2$ concentration and a first pH value, the first $CO_2$ concentration being a $CO_2$ concentration of a first gas volume above a medium in a first tank, the first $CO_2$ concentration and the first pH value being measured at a first time, the first time being a time when the medium in the first tank is in pH-$CO_2$ equilibrium state with the first gas volume at a predefined temperature and pressure, said equilibrium state being unaffected by the metabolism of any cell culture, the first pH value being a measured value provided by a first pH measuring device;
receive a second $CO_2$ concentration and a second pH value, the second $CO_2$ concentration being a $CO_2$ concentration of a second gas volume above the same type of medium contained in a second tank, the second $CO_2$ concentration and the second pH value being measured at a second time, the second time being a time when the medium in the second tank is in pH-$CO_2$ equilibrium state with the second gas volume at the predefined temperature and pressure, said equilibrium state being unaffected by the metabolism of any cell culture, the second pH value being a measured value provided by a second pH measuring device;
compare the first and second pH values and comparing compare the first and second $CO_2$ concentrations for determining that the first pH measuring device is affected by a pH measuring problem;
calibrate the first pH measuring device based on determining that the first pH measuring device is affected by the pH measuring problem, the problem being that the first pH measuring device operatively coupled to the first tank is calibrated differently than the second pH measuring device operatively coupled to the second tank; and cause measurement of a calibrated first pH value using the calibrated first pH measuring device.

\* \* \* \* \*

UNITED STATES PATENT AND TRADEMARK OFFICE
CERTIFICATE OF CORRECTION

PATENT NO. : 11,866,686 B2
APPLICATION NO. : 17/575008
DATED : January 9, 2024
INVENTOR(S) : Eisenkraetzer et al.

It is certified that error appears in the above-identified patent and that said Letters Patent is hereby corrected as shown below:

In the Claims

Column 48,
Lines 60 and 61, "comparing compare" should read --compare--.

Signed and Sealed this
Fourteenth Day of May, 2024

Katherine Kelly Vidal
*Director of the United States Patent and Trademark Office*